(12) United States Patent
Hogenkamp et al.

(10) Patent No.: US 7,820,663 B2
(45) Date of Patent: Oct. 26, 2010

(54) SUBSTITUTED ENAMINONES, THEIR DERIVATIVES AND USES THEREOF

(75) Inventors: Derk J. Hogenkamp, Carlsbad, CA (US); Timothy B. C. Johnstone, Costa Mesa, CA (US); Kelvin W. Gee, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 1095 days.

(21) Appl. No.: 11/455,228

(22) Filed: Jun. 15, 2006

(65) Prior Publication Data

US 2006/0293329 A1   Dec. 28, 2006

Related U.S. Application Data

(60) Provisional application No. 60/691,934, filed on Jun. 17, 2005.

(51) Int. Cl.
*C07D 401/02* (2006.01)
*A61K 31/47* (2006.01)

(52) U.S. Cl. ............... 514/247; 514/252.1; 514/255.05; 514/257; 514/310; 514/311; 514/352; 514/359; 514/364; 514/381; 514/383; 514/372; 514/378; 514/374; 514/406; 544/224; 544/329; 544/406; 546/146; 546/159; 546/304; 548/133; 548/143; 548/212; 548/222; 548/253; 548/268.4; 548/367.4

(58) Field of Classification Search ............... None
See application file for complete search history.

(56) References Cited

FOREIGN PATENT DOCUMENTS

| DE | 294250 A5 * | 9/1991 | |
|---|---|---|---|
| WO | WO 2004/052889 A1 | 6/2004 | ............... 453/2 |
| WO | WO 2004/085433 A2 | 10/2004 | |
| WO | WO 2005/108347 A2 | 11/2005 | |

OTHER PUBLICATIONS

Eiden et al, Archiv der Pharmazie, 1986, 319(3), pp. 242-251.*
West, Anthony R., Solid State Chemistry and its Applications, Wiley, New York, 1988, pp. 358 & 365.*
Hauser et al, Journal fuer Praktische Chemie (Leipzig) (1977), 319(2), pp. 263-273.*
Fischer, et al, Journal of Heterocyclic Chemistry (1996), 33(3), pp. 815-823.*
English Translation of DD 294250 A5, Fischer et al, Sep. 1991.*
Dains, et al., "The Reactions of the Formamidines. III. On the Synthesis of Isoxazole, Cyanoacetic and Benzoylacetic Derivatives", J. Am. Chem. Soc., vol. 35, 1913, pp. 959-970.
Dains, et al., "On the Reactions of the Formamidines. V. On Some Pyrazolone Derivatives", J. Am. Chem. Soc., vol. 38, 1916, pp. 1510-1517.
Goerdeier J., et al., "Herstellung Und Konformation Von Vinylogen Harnstoffen Preparation and Conformation of Vinylogous Ureas" vol. 113, No. 7, 1980, pp. 2499-2508.
Moszew, et al., "Reaction of Diphenylformamidine with Anilides of beta-ketoacids. Part 1", vol. 14, 1969, pp. 89-94.

* cited by examiner

*Primary Examiner*—Zinna N Davis
(74) *Attorney, Agent, or Firm*—Cooley LLP

(57) ABSTRACT

The present invention is related substituted enaminones represented by a compound of Formula I that are novel allosteric modulators of $\alpha 7$ nAChRs. The invention also discloses the treatment of disorders that are responsive to enhancement of acetylcholine action on $\alpha 7$ nAChRs in a mammal by administering an effective amount of a compound of Formula I.

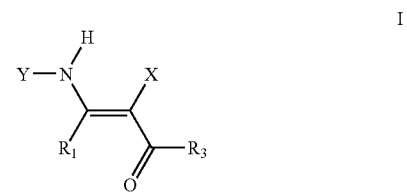

44 Claims, No Drawings

SUBSTITUTED ENAMINONES, THEIR DERIVATIVES AND USES THEREOF

CROSS REFERENCE TO RELATED APPLICATIONS

This application claims the benefit of U.S. Provisional Application No. 60/691,934, filed Jun. 17, 2005, which is incorporated herein in its entirety.

FIELD OF THE INVENTION

This invention is in the field of medicinal chemistry. In particular, the invention relates to substituted enaminones and their derivatives and the discovery that these compounds allosterically modulate the nicotinic acetylcholine receptor (nAChR) in a therapeutically relevant fashion and may be used to ameliorate CNS disorders amenable to modulation of the nAChR.

BACKGROUND OF THE INVENTION

α7 nAChRs belong to the ligand-gated ion channel superfamily of Cys-loop receptors. The Cys-loop superfamily includes muscle and neuronal nAChRs, 5-hydroxytryptamine type 3 (5HT$_3$), γ-aminobutyric acid$_A$ (GABA$_A$), GABA$_C$ and glycine receptors. α7 nAChRs are allosteric proteins which recognize acetylcholine and choline as the orthosteric ligand and bind nicotine at the orthosteric site. Neuronal α7 nAChRs contain 5 orthosteric sites per receptor. Agonist binding to the orthosteric site transmits an allosteric effect which modulates the functional states of the receptor depending on the concentration and kinetics of agonist application. Four functional states have been described for nAChRs: one open and three closed states (resting, fast-onset desensitized, slow-onset desensitized). Activation of neuronal nAChRs mediates fast synaptic transmission and controls synaptic transmission by the major inhibitory and excitatory neurotransmitters, GABA and glutamate.

α7 nAChRs mediate the predominant nicotinic current in hippocampal neurons. The α7 nAChR was initially identified from a chick brain library as an α-bungarotoxin binding protein that exhibits ~40% sequence homology to other nAChRs. α7 nAChRs share similar features of other neuronal and muscle nAChRs such as a pentameric Cys-loop receptor structure and M2 segment of each subunit lining of the channel pore, however the α7 nAChR exhibits a homopentameric structure when reconstituted in *Xenopus* oocytes, a characteristic shared only with the α8 and α9 nAChRs. Heterologously expressed homomeric α7 nAChRs in *Xenopus* oocytes are inactivated by α-bungarotoxin with high affinity, whereas other nAChRs are not. α7 nAChRs have also been pharmacologically identified by distinct types of whole cell currents elicited by nicotinic agonists in hippocampal neurons. When exposed to various nicotinic agonists whole cell recordings from cultured hippocampal neurons show, in general, type IA currents that have a very brief open time, high conductance, very high $Ca^{++}$ permeability, decay rapidly, and are sensitive to blockade by MLA and α-bungarotoxin. The properties of these nicotinic currents in hippocampal neurons correspond to the currents mediated by α7 nAChRs expressed in oocytes. We are specifically interested in α7 nAChRs because of their role in regulating fast synaptic transmission in the hippocampus where it provides a specific target for the modulation of hippocampal function.

RELATED ART

The following compounds have been disclosed:

A: Kussler, M. Dyes and Pigments, 1987, 8(3), 179-187;

Compounds B and B' have registry numbers, but have no literature references (R=Me, Cl, OMe);

C: Walter, W. and Fleck, T. Justus Liebigs Annalen der Chemie, 1976, 4, 670-81 (R=H and MeO);

D: Hauser et al. (Journal fuer Praktische Chemie (Leipzig) 1977, 319(2), 263); and E: Archiv. der Pharmazie (Weinheim, Ger.) 1986, 319(3), 242 (R=H, OMe).

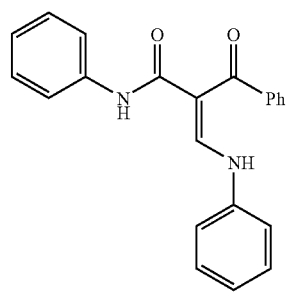

A

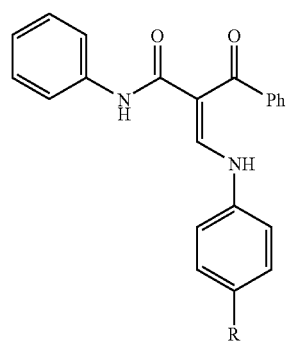

B

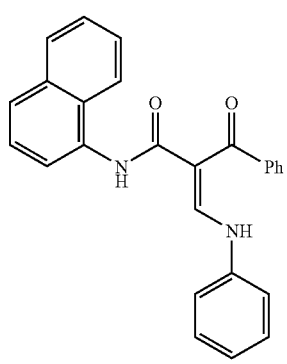

B'

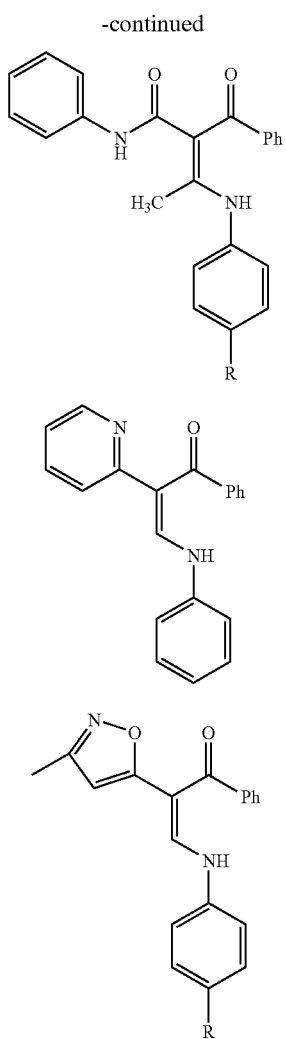

SUMMARY OF THE INVENTION

The present invention is related to the discovery that certain substituted enaminones represented by compounds of Formulae I-VII act as novel allosteric modulators of α7 nAChRs.

The invention is related with treating disorders responsive to enhancement of acetylcholine action on α7 nAChRs in a mammal by administering an effective amount of a compound of Formulae I-VII as described herein.

Without being bound by any theory proposed herein, it is believed that the compounds of the present invention, being ligands for α7 nAChRs, are therefore of use in the treatment and/or prevention of a variety of disorders of the central nervous system (CNS). Such disorders of the CNS include neurodegenerative diseases, senile dementias and schizophrenia.

In one aspect, the present invention is directed to the use of the compounds of Formulae I-VII as enhancers of acetylcholine-facilitated monovalent and divalent cation flux mediated through the α7 nAChR. Also, an aspect of the present invention is to provide a pharmaceutical composition useful for treating disorders responsive to the enhancement of acetylcholine-facilitated monovalent and divalent cation mediated flux through the nAChR, containing an effective amount of a compound of Formulae I-VII in a mixture with one or more pharmaceutically acceptable carriers or diluents.

Another aspect of the present invention is directed to the use of the compounds of Formulae I-VII as ligands for $GABA_A$ receptors, are therefore of use in the treatment and/or prevention of a variety of disorders of the central nervous system (CNS). In one aspect, the compounds are useful for the treatment and/or prevention of disorders of the CNS involving neuronal hyperexcitability. Such disorders include but are not limited to anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder, neuroses, convulsions, migraine, and depressive or bipolar disorders, for example single-episode or recurrent major depressive disorder, dysthymic disorder, bipolar I and bipolar II manic disorders, and cyclothymic disorder.

Yet another aspect of the present invention is directed to the use of the compounds of Formulae I-VII as enhancers of GABA-facilitated Cl⁻ flux mediated through the $GABA_A$ receptor complex. Also, an aspect of the present invention is to provide a pharmaceutical composition useful for treating disorders responsive to the enhancement of GABA-facilitated Cl⁻ flux mediated through the GRC, containing an effective amount of a compound of Formulae I-VII in a mixture with one or more pharmaceutically acceptable carriers or diluents.

In another aspect, the present invention is directed to the use of the compounds of Formulae I-VII as enhancers of both GABA-facilitated Cl⁻ flux mediated through the $GABA_A$ receptor complex and acetylcholine-facilitated monovalent and divalent cation flux mediated through the α7 nAChR.

Compounds useful in the present invention have not been heretofor reported. Thus, the present invention is also directed to novel substituted enaminones having the structures of Formulae I-VII. Further, the present invention is directed to $^3H$, $^{11}C$, $^{18}F$, $^{35}S$, $^{36}Cl$, $^{14}C$ and $^{125}I$ radiolabeled compounds of Formulae I-VII and their use as radioligands for their binding site on the nAChR and/or the $GABA_A$ receptor complex. Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The compounds useful in this aspect of the invention are substituted enaminones represented by Formula I:

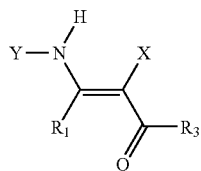

or a pharmaceutically acceptable salt, prodrug or solvate thereof, wherein:

X is selected from the group consisting of:

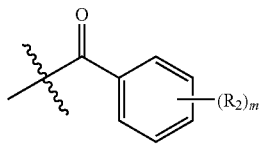

where m is 0 to 5;

an optionally substituted heteroaromatic ring (HET) selected from the group consisting of:

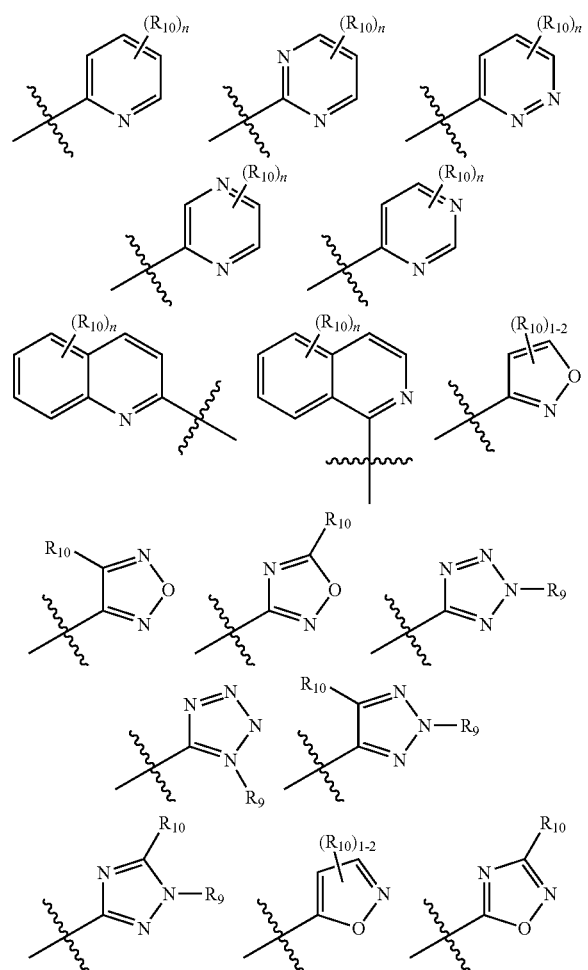

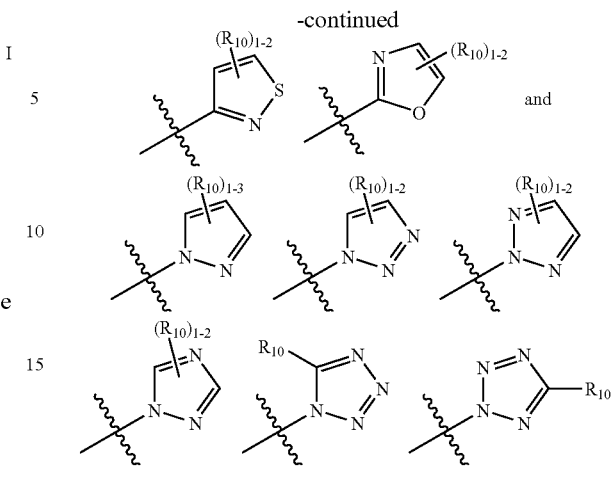

wherein:

n is 0-3;

Y is selected from the group consisting of aryl and heteroaryl, and a dialkylamino group, each unsubstituted or substituted;

$R_1$ is selected from the group consisting of hydrogen and substituted or unsubstituted $C_{1-10}$alkyl;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_3$ is selected from the group consisting of arylamino, heteroarylamino and aryl, each unsubstituted or substituted; and each $R_9$ is independently selected from the group consisting of hydrogen, $C_{1-10}$alkyl, aralkyl, aryl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

with the proviso that the compound is not α-[(phenylamino)methylene]-β-oxo-N-phenylbenzenepropanamide, α-[1-(phenylamino)ethylidene]-β-oxo-N-phenylbenzenepropanamide, α-[1-[(4-methoxyphenyl)amino]ethylidene]-β-oxo-N-phenylbenzenepropanamide, 1-phenyl-3-phenylamino-2-(3-methyl-5-isoxazolyl)-2-propen-1-one, 3-[(4-methoxyphenyl)amino]-2-(3-methyl-5-isoxazolyl)-1-phenyl-2-propen-1-one and 1-phenyl-3-phenylamino-2-(2-pyridyl)-2-propen-1-one and that when X is the group:

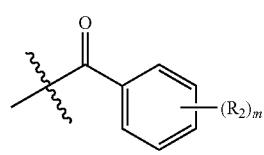

$R_3$ is unsubstituted or substituted arylamino.

The compounds useful in this aspect of the invention are substituted enaminones represented by Formula II:

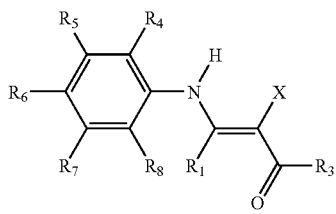

or a pharmaceutically acceptable salt, prodrug or solvate thereof, wherein:

X is selected from the group consisting of:

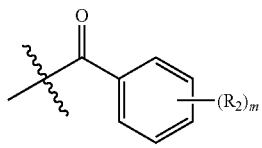

where m is 0 to 5;

an optionally substituted heteroaromatic ring (HET) selected from the group consisting of:

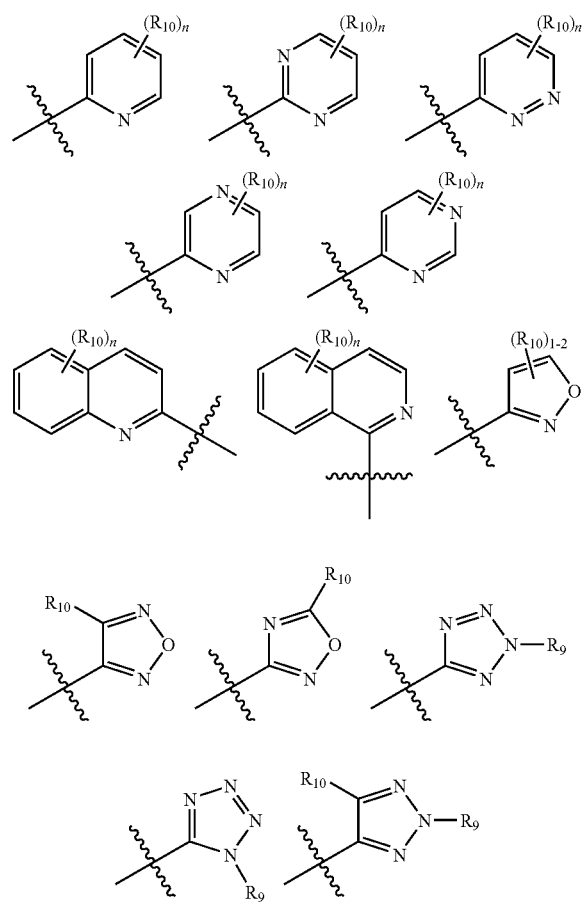

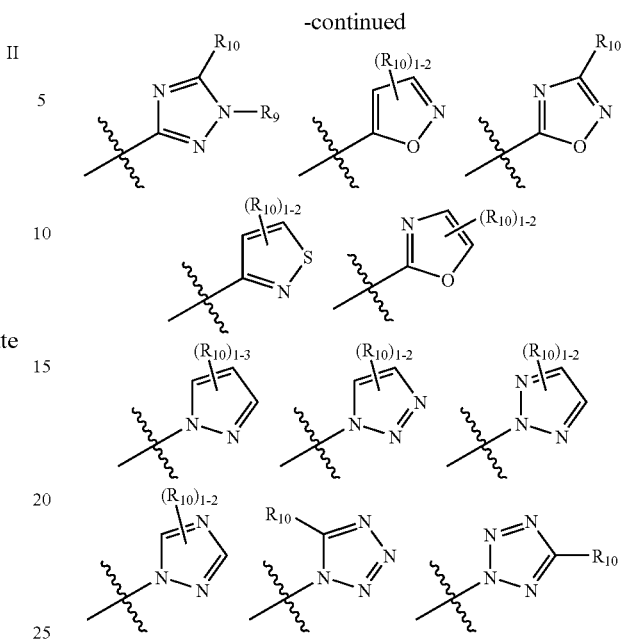

n is 0-3;

$R_1$ is selected from the group consisting of hydrogen and substituted or unsubstituted $C_{1-10}$alkyl;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_3$ is selected from the group consisting of arylamino, heteroarylamino and aryl, each unsubstituted or substituted;

$R_4$, $R_5$, $R_6$, $R_7$ and $R_8$ are each independently selected from the group consisting of hydrogen, halo, halo$C_{1-10}$alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interupted by one —O—, —NR—, —S—, —SO— or —SO$_2$—, aryl or heteroaryl, where R is hydrogen or unsubstituted or substituted $C_{1-10}$alkyl; and each $R_9$ is independently selected from the group consisting of hydrogen, $C_{1-10}$alkyl, aralkyl, aryl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

with the proviso that the compound is not α-[(phenylamino)methylene]-β-oxo-N-phenylbenzenepropanamide, α-[1-(phenylamino)ethylidene]-β-oxo-N-phenylbenzenepropanamide, α-[1-[(4-methoxyphenyl)amino]ethylidene]-β-oxo-N-phenylbenzenepropanamide, 1-phenyl-3-phenylamino-2-(3-methyl-5-isoxazolyl)-2-propen-1-one, 3-[(4-methoxyphenyl)amino]-2-(3-methyl-5-isoxazolyl)-1-phenyl-2-propen-1-one and 1-phenyl-3-phenylamino-2-(2-pyridyl)-2-propen-1-one and that when X is the group:

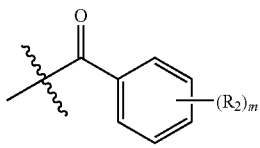

$R_3$ is unsubstituted or substituted arylamino.

Additional compounds useful in this aspect of the invention are substituted enaminones represented by Formula III:

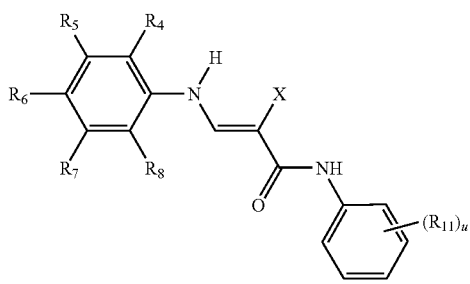

or a pharmaceutically acceptable salt, prodrug or solvate thereof, wherein:

u is 1-5; and $R_4$-$R_8$ and X are defined previously with respect to Formula II; and each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

with the proviso that the compound is not α-[(phenylamino)methylene]-β-oxo-N-phenylbenzenepropanamide, α-[1-(phenylamino)ethylidene]-β-oxo-N-phenylbenzenepropanamide, and α-[1-[(4-methoxyphenyl)amino]ethylidene]-β-oxo-N-phenylbenzenepropanamide.

Additional compounds useful in this aspect of the invention are substituted enaminones represented by Formula IV:

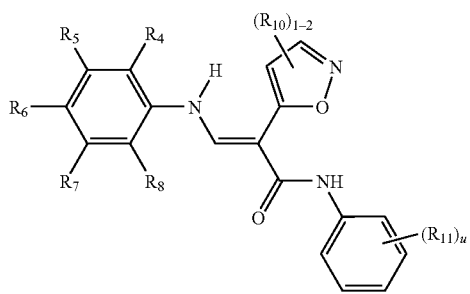

or a pharmaceutically acceptable salt, prodrug or solvate thereof, wherein:

$R_4$, $R_5$, $R_6$, $R_7$ and $R_8$ are each independently selected from the group consisting of hydrogen, halo, halo$C_{1-10}$alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interupted by one —O—, —NR—, —S—, —SO— or —SO$_2$—, aryl or heteroaryl, where R is hydrogen or unsubstituted or substituted $C_{1-10}$alkyl;

each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and u is 1-5.

Additional compounds useful in this aspect of the invention are substituted enaminones represented by Formula V:

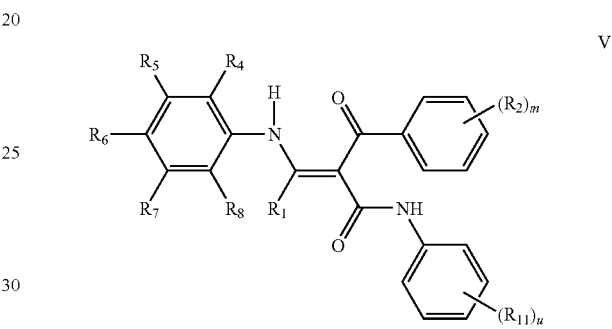

or a pharmaceutically acceptable salt, prodrug or solvate thereof, wherein:

$R_1$ is hydrogen or methyl;

$R_2$, $R_4$-$R_8$ and $R_{11}$ are defined previously with respect to Formula IV;

with the proviso that the compound is not α-[(phenylamino)methylene]-β-oxo-N-phenylbenzenepropanamide, α-[1-(phenylamino)ethylidene]-β-oxo-N-phenylbenzenepropanamide or α-[1-[(4-methoxyphenyl)amino]ethylidene]-β-oxo-N-phenylbenzenepropanamide.

Additional compounds useful in this aspect of the invention are substituted enaminones represented by Formula VI:

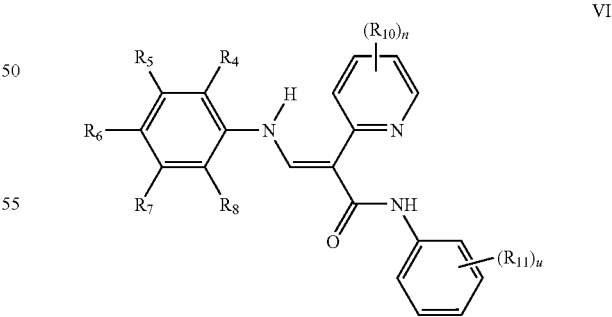

or a pharmaceutically acceptable salt, prodrug or solvate thereof, wherein:

$R_4$, $R_5$, $R_6$, $R_7$ and $R_8$ are each independently selected from the group consisting of hydrogen, halo, halo$C_{1-10}$alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interupted by one —O—, —NR—, —S—, —SO— or —SO$_2$—, aryl or heteroaryl, where R is hydrogen or unsubstituted or substituted $C_{1-10}$alkyl;

each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; n is 0 to 3; and u is 1 to 5.

Additional compounds useful in this aspect of the invention are substituted enaminones represented by Formula VII:

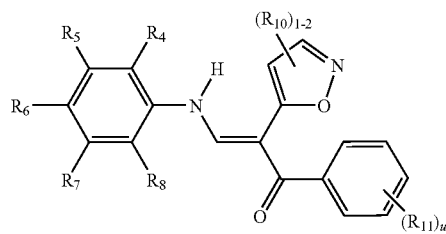

VII or a pharmaceutically acceptable salt, prodrug or solvate thereof, wherein:

$R_4$, $R_5$, $R_6$, $R_7$ and $R_8$ are each independently selected from the group consisting of hydrogen, halo, halo$C_{1-10}$alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO— or —SO$_2$—, aryl or heteroaryl, where R is hydrogen or unsubstituted or substituted $C_{1-10}$alkyl;

each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and u is 1-5;

with the proviso that the compound is not 3-(phenylamino)-2-(3-methyl-5-isoxazolyl)-1-phenyl-2-propen-1-one and 3-[(4-methoxyphenyl)amino]-2-(3-methyl-5-isoxazolyl)-1-phenyl-2-propen-1-one.

Preferred compounds from Formulae I-VII include:
3-[(4-ethoxyphenyl)amino]-2-(3-methyl-5-isoxazolyl)-1-phenyl-2-propen-1-one;
3-[(4-hydroxyphenyl)amino]-2-(3-methyl-5-isoxazolyl)-1-phenyl-2-propen-1-one;
3-[(4-chlorophenyl)amino]-2-(3-methyl-5-isoxazolyl)-1-phenyl-2-propen-1-one;
1-(2-chlorophenyl)-3-[(4-ethoxyphenyl)amino]-2-(3-methyl-5-isoxazolyl)-2-propen-1-one;
1-(4-chlorophenyl)-3-[(4-ethynylphenyl)amino]-2-(3-methyl-5-isoxazolyl)-2-propen-1-one;
1-(4-chlorophenyl)-3-[(4-chlorophenyl)amino]-2-(3-methyl-5-isoxazolyl)-2-propen-1-one; and
1-(2-chlorophenyl)-3-[(4-chlorophenyl)amino]-2-(3-methyl-5-isoxazolyl)-2-propen-1-one.

More preferred compounds of Formulae I-VII include:
α-[[(4-ethoxyphenyl)amino]methylene]-β-oxo-N-phenyl-benzenepropanamide;
α-[[(4-iodophenyl)amino]methylene]-3-methyl-N-phenyl-5-isoxazoleacetamide;
α-[[(4-ethoxyphenyl)amino]methylene]-3-methyl-N-phenyl-5-isoxazoleacetamide;
N-(4-chlorophenyl)-α-[[(4-ethoxyphenyl)amino]methylene]-3-methyl-5-isoxazoleacetamide;
N-(3-chlorophenyl)-α-[[(4-ethoxyphenyl)amino]methylene]-3-methyl-5-isoxazoleacetamide;
N-(2-chlorophenyl)-α-[[(4-ethoxyphenyl)amino]methylene]-3-methyl-5-isoxazoleacetamide;
N-(4-chlorophenyl)-α-[[(4-chlorophenyl)amino]methylene]-3-methyl-5-isoxazoleacetamide;
N-(4-chlorophenyl)-α-[(3-fluorophenylamino)methylene]-3-methyl-5-isoxazoleacetamide;
N-(4-chlorophenyl)-α-[(1H-indol-5-ylamino)methlene]-3-methyl-5-isoxazoleacetamide;
N-(4-chlorophenyl)-α-[(3-hydroxylphenylamino)methylene]-3-methyl-5-isoxazoleacetamide;
N-(4-chlorophenyl)-α-[(isoquinolin-5-ylamino)methylene]-3-methyl-5-isoxazoleacetamide;
N-(4-chlorophenyl)-α-[(indazol-6-ylamino)methylene]-3-methyl-5-isoxazoleacetamide;
N-(4-chlorophenyl)-α-[(indazol-5-ylamino)methylene]-3-methyl-5-isoxazoleacetamide;
N-(4-chlorophenyl)-α-[(3-methylisoxazol-5-ylamino)methylene]-3-methyl-5-isoxazoleacetamide;
N-(4-chlorophenyl)-3-methyl-α-[(5-methylisoxazol-3,-ylamino)methylene]-5-isoxazoleacetamide;
N-(4-fluorophenyl)-3-methyl-α-[(5-methylisoxazol-3-ylamino)methylene]-5-isoxazoleacetamide;
N-(4-chlorophenyl)-3-methyl-α-[(4-nitrophenylamino)methylene]-5-isoxazoleacetamide;
N-(4-chlorophenyl)-α-[[(4-dimethylamino)phenylamino]methylene]-3-methyl-5-isoxazoleacetamide;
N-(4-fluorophenyl)-α-[(4-fluorophenylamino)methylene]-3-methyl-5-isoxazoleacetamide;
α-[(4-ethylphenylamino)methylene]-N-(4-fluorophenyl)-3-methyl-5-isoxazoleacetamide;
N-(4-fluorophenyl)-3-methyl-α-[(4-methylphenylamino)methylene]-5-isoxazoleacetamide;
N-(4-chlorophenyl)-α-[[4-(chlorophenyl)amino]methylene]-5-methyl-3-isoxazoleacetamide;
N-(4-chlorophenyl)-α-[[4-(fluorophenyl)amino]methylene]-5-methyl-3-isoxazoleacetamide;
N-(4-chlorophenyl)-α-[[4-(hydroxyphenyl)amino]methylene]-5-methyl-3-isoxazoleacetamide;
N-(4-chlorophenyl)-α-[(3-pyridylamino)methylene]-5-methyl-3-isoxazoleacetamide;
N-(4-fluorophenyl)-α-[(3-pyridylamino)methylene]-5-methyl-3-isoxazoleacetamide;
α-[4-(chlorophenylamino)methylene]-3-methyl-N-(4-pyridyl)-5-isoxazoleacetamide;
α-[(3-azabicyclo[3.3.0]octyl-3-amino)methylene]-N-(4-chlorophenyl)-3-methyl-5-isoxazoleacetamide;
α-[4-(chlorophenylamino)methylene]-3-methyl-N-(2-pyridyl)-5-isoxazoleacetamide; and α-[4-(chlorophenylamino)methylene]-3-methyl-N-(3-pyridyl)-5-isoxazoleacetamide In one aspect, there is provided a pharmaceutical composition, comprising a compound having Formulae I-VII. In another aspect, there is provided a method for the treatment of CNS disorders amenable to modulation of the nAChR complex which comprises administering to a patient in need of such treatment a compound of the above Formulae I-VII or a pharmaceutically acceptable salt, prodrug or solvate thereof. In one variation of the above method, the CNS disorder is a neurodegenerative disorder. In another variation, the CNS disorder is a senile dementia. In another variation, the CNS disorder is schizophrenia. In another variation of the method, the CNS disorder is a cognition deficit disorder.

In another aspect, there is provided a method for the treatment of CNS disorders related to, learning and memory such as mild cognitive impairment, age related cognitive decline, senile dementia, and Alzheimer's disease by inhibition of mono and divalent cation conductance through the site mediating the action of a compound of Formulae I-VII which comprises administering to a patient in need of such treatment a compound of Formulae I-VII or a pharmaceutically acceptable salt, prodrug or solvate thereof.

In another aspect, there is provided a method for the treatment of CNS disorders amenable to modulation of the $GABA_A$ receptor complex which comprises administering to a patient in need of such treatment a compound of Formulae I-VII. In one variation of the method, the CNS disorder is an anxiety disorder. In another variation, the CNS disorder is convulsions. In yet another variation, the CNS disorder is insomnia. In another variation, the CNS disorder is a major depressive or bipolar disorder. In yet another variation of the method, the CNS disorder is chronic or acute pain, or the CNS disorder is a neuroses. In yet another variation of the above-method, the CNS disorder is withdrawal-induced convulsions from substance abuse, or the CNS disorder is a phobia. In another variation of the method, the CNS disorder is a panic disorder. In a particular variation of the method, the CNS disorder is a generalized anxiety disorder.

In another variation of the above method, the CNS disorder is an obsessive-compulsive disorder. In another particular variation, the CNS disorder is a post traumatic and acute stress disorder, or the CNS disorder is a migraine. In another variation, the CNS disorder is a bipolar manic disorder. In another variation of the above method, the CNS disorder is selected from the group consisting of anxiety and stress related disorders, depression and other affective disorders, epilepsy and other seizure disorders, insomnia and related sleep disorders, acute and chronic pain and cough. In one variation of the above method, the sleep disorder involving reduced wakefulness is selected from the group consisting of narcolepsy and idiopathic hypersomnia.

In one variation of the above method, the compound of Formulae I-VII or a pharmaceutically acceptable salt thereof acts by binding to a site that is not the site that binds [$^3$H]-flunitrazepam, barbiturates, loreclezole, [$^3$H]-muscimol or 3α,20α-pregnanediol thereby altering chloride conductance through the $GABA_A$ receptor complex in a therapeutically usefully fashion. In another aspect, there is provided a method for the treatment of CNS disorders which comprises administering to a patient in need of such treatment a compound of Formulae I-VII with allosteric modulatory activity at both $GABA_A$ and α7 nAChR receptors. In yet another aspect, there is provided a method for the treatment of CNS disorders which comprises administering to a patient in need of such treatment a compound of Formula I, II, III, IV, V, VI or VII, or a pharmaceutically acceptable salt thereof, with activity for positive allosteric modulation of currents at α7 nAChR receptors in which modulated currents retain the rapid native kinetics and native desensitization of the receptor observed in the absence of a compound of Formula I, II, III, IV, V, VI or VII.

For use in medicine, the salts of the compounds of Formulae I-VII will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, or phosphoric acid. Furthermore, where the compounds of the invention comprises an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

The present invention includes within its scope prodrugs of the compounds of Formulae I-VII above. In general, such prodrugs will be functional derivatives of the compounds of Formulae I-VII that are readily convertible in vivo into the required compound of Formulae I-VII. Conventional procedures for the selection and preparation of suitable prodrug derivatives are described, for example, in Design of Prodrugs, ed. H. Bundgaard, Elsevier, 1985.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. Where the compounds according to the invention possess geometrical isomers, all such isomers and mixtures thereof in any proportion are encompassed within the scope of the present invention.

Useful halogen groups include fluorine, chlorine, bromine and iodine.

"Alkyl" means a straight or branched, saturated or unsaturated aliphatic radical with the number of carbon atoms depicted. An alkyl group may comprise a heteroatom, such as an oxygen, nitrogen or sulfur inserted within or in the chain of the alkyl group. Useful alkyl groups include straight chain and branched $C_{1-20}$alkyl groups, more preferably, $C_{1-10}$alkyl groups. Typical $C_{1-10}$alkyl groups include methyl, ethyl, n-propyl, isopropyl, n-butyl, sec-butyl, iso-butyl, 1,2-dimethylpropyl, n-pentyl, 2-pentyl, 3-pentyl, n-hexyl, n-heptyl, n-octyl, n-nonyl and n-decyl groups. An alkyl group may also be represented with another group, such as an "arylalkyl" group, such as a benzyl group.

An "aryl" group may be a monocyclic, bicyclic or polycyclic ring system wherein each ring is aromatic, or when fused or connected to one or more rings to form a polycyclic ring system. An aryl ring may also be fused with a non-aromatic ring. An aryl ring may also contain a heteroatom to form a hetroaryl ring. Useful aryl groups are $C_{6-14}$aryl, especially C$_{6-10}$aryl. Typical C$_{6-14}$aryl groups include phenyl, naphthyl, anthracenyl, indenyl and biphenyl groups.

An "arylalkyl" or "aralkyl" group includes any of the above-mentioned C$_{1-20}$alkyl groups substituted with any of the above-mentioned C$_{6-10}$aryl groups. Similarly, a substituted C$_{1-10}$alkyl may also represent an arylalkyl or aralkyl group (or heteroarylalkyl, etc . . . ) when the C$_{1-10}$alkyl group is substituted with an aryl group. Useful arylalkyl groups include any of the above-mentioned C$_{1-20}$alkyl groups substituted with any of the above-mentioned C$_{6-10}$aryl groups. Useful arylalkyl groups include benzyl and phenethyl.

Useful cycloalkyl groups include cyclopropyl, cyclobutyl, cyclopentyl, cyclohexyl, cycloheptyl and cyclooctyl groups.

Useful cycloalkylalkyl groups include any of the above-mentioned C$_{1-20}$alkyl groups substituted with any of the previously mentioned cycloalkyl groups. Examples of useful cycloalkylalkyl groups include cyclohexylmethyl and cyclopropylmethyl groups.

Useful haloalkyl groups include C$_{1-20}$alkyl groups substituted with one or more fluorine, chlorine, bromine or iodine atoms, including for example, fluoromethyl, difluoromethyl, trifluoromethyl and 1,1-difluoroethyl groups. A haloalkyl group also includes perhaloalkyl groups, which include, for example, trifluoromethyl and pentafluoroethyl groups.

Useful hydroxyalkyl groups include C$_{1-20}$alkyl groups substituted by hydroxy, including hydroxymethyl, 1- and 2-hydroxyethyl and 1-hydroxypropyl groups.

Useful alkoxy groups include oxygen substitution by one of the C$_{1-20}$alkyl groups described above.

Useful alkylthio groups include sulfur substitution by one of the C$_{1-20}$alkyl groups described above including, for example, methyl- and ethylthio groups.

An "amino" group is —NH$_2$. Alkylamino and dialkylamino groups, for example, include the groups —NHR$_{12}$ and —NR$_{12}$R$_{13}$, wherein each R$_{12}$ and R$_{13}$ are independently substituted or unsubstituted C$_{1-20}$alkyl groups. Example of such groups include —NHMe, —NHEt, —NHcyclohexyl, —NHCH$_2$phenyl, —N(Me)$_2$, and the like. Useful dialkylaminoalkyl groups include any of the above-mentioned C$_{1-10}$alkyl groups, each substituted or unsubstituted. Also, a substituted amino group may include for example, —NHMe, —NHEt, —NHcyclohexyl, —N(Me)$_2$ and the like, and —NHCOMe, —NHCOEt, —NHCONHMe, and the like. Useful alkylamino and dialkylamino are —NHR$_{12}$ and —NR$_{12}$R$_{13}$, wherein R$_{12}$ and R$_{13}$ are C$_{1-20}$alkyl groups, each unsubstituted or substituted by any of the previously mentioned dialkylamino groups. A dialkylamino group, such as —NR$_{12}$R$_{13}$, includes the group wherein R$_{12}$ and R$_{13}$ are combined with the nitrogen to which they attach to form a ring, such as a 3-membered, 4-membered, 5-membered or 6-membered ring and their fused, bicyclic analogs, each of which may be further substituted as defined herein. Non-exclusive examples of such rings may include azirines, pyrrolidines, piperidines and the like. In certain variations of the nitrogen containing ring, the ring may comprise one or more double bonds and may be fully or partially unsaturated.

Useful alkylthiol groups include any of the above-mentioned C$_{1-20}$ alkyl groups substituted by a —SH group.

A carboxy group is —COOH.

The term heterocyclic is used herein to mean saturated or partially unsaturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or nitrogen if the resulting compound is stable. Examples include, but are not limited to pyrrolidine, piperidine, piperazine, morpholine, 1,2,3,4-tetrahydroquinoline, and the like.

The term heteroaryl is used herein to mean wholly unsaturated 5 and 6 membered monocyclic, or 9 and 10 membered bicyclic ring system, which consists of carbon atoms and from one to four heteroatoms independently selected from the group consisting of O, N, and S, wherein the nitrogen and sulfur heteroatoms can be optionally oxidized, for example, to form —N(O)—, —SO—, SO$_2$—, the nitrogen can be optionally quaternized; and including any bicyclic group in which any of the above-defined heterocyclic rings is fused to a benzene ring, and wherein the heteroaryl ring can be substituted on carbon or nitrogen if the resulting compound is stable. Examples include, but are not limited to pyridine, pyrimidine, pyradizine, tetrazole, imidazole, isoxazole, oxazole, 1,2,4-oxadiazole, 1,2,3-oxadiazole, quinoline, and the like.

The term "heteroarylamino group" is an —NH-heteroaryl group.

"Isomers" mean any compound with an identical molecular formula but having a difference in the nature or sequence of bonding or arrangement of the atoms in space. Examples of such isomers include, for example, E and Z isomers of double bonds, enantiomers, and diastereomers. Compounds of the present invention depicting a bond with a straight line or "squiggly line" representation that is attached to a double bond, unless specifically noted otherwise, is intended to encompass a single isomer and/or both isomers of the double bond as shown below.

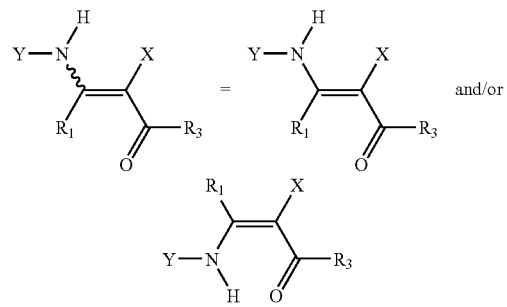

"Substituted or unsubstituted" means that a group may consist of only hydrogen substituents (unsubstituted) or may further comprise one or more non-hydrogen substituents (substituted) that are not otherwise specified. For example, tert-butyl group may be an example of a propyl group that is substituted by a methyl group. Examples of substituents include, but are not limited to, C$_{1-10}$alkyl, C$_{2-10}$alkylene, amide, amino, aryl, carbamoyl, carbonyl group, cycloalkyl, ester, halo, heteroaryl, oxo, hydroxy or nitro groups, each of which may also be substituted or unsubstituted as valency permits. Optional substituents on R$_1$ to R$_{13}$ include any one of halo, halo(C$_{1-20}$)alkyl, aryl, aryloxy, heteroaryl, heteroaryloxy, cycloalkyl, cycloalkyloxy, C$_{1-20}$alkyl, aryl(C$_{1-20}$)alkyl, cycloalkyl(C$_{1-20}$)alkyl, hydroxy(C$_{1-20}$)alkyl, amino(C$_{1-20}$) alkyl, alkoxy(C$_{1-20}$)alkyl, amino, hydroxy, cyano, nitro, thiol, C$_{1-20}$alkoxy and C$_{1-20}$alkylthiol groups mentioned above. Preferred optional substituents include: halo, halo(C$_{1-6}$)alkyl, amino(C$_{1-6}$)alkyl, alkoxy, hydroxy and amino.

The preparation of the compounds of the present invention may be performed using the standard methods know in the art of organic synthesis. Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, *Protecting Groups in Organic Synthesis*, 3rd edition, John Wiley & Sons, Inc. 1999.

Compounds of Formula I were prepared as shown in Schemes 1 and 2, starting with commercially available heteroaromatic acetic acids or 3,5-dimethylisoxazole (Aldrich), respectively. Reaction with ethyl formate was carried out according to the procedure of Bertolini, et al. *J. Org. Chem.* 1996, 61, 3358-3361. The anion formed from 3,5-dimethylisoxazole and nBuLi in Scheme 2 can also be quenched with arylisocyanates as another method for the synthesis of N-aryl-3-methyl-5-isoxazoleacetamides (Burkhart, et al. *Tetrahedron* 2001, 57, 8039 and Zhou, et al. *Tetrahedron Lett.* 1998, 39, 8249).

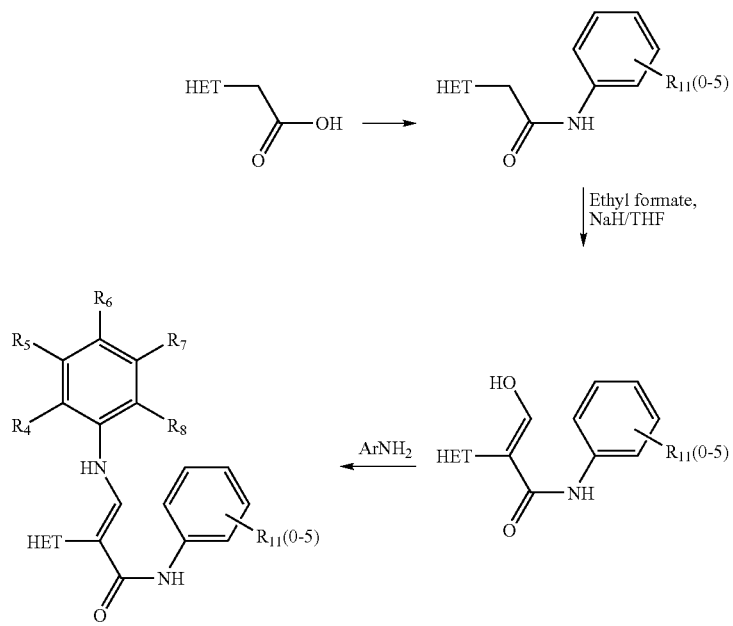

Scheme 1

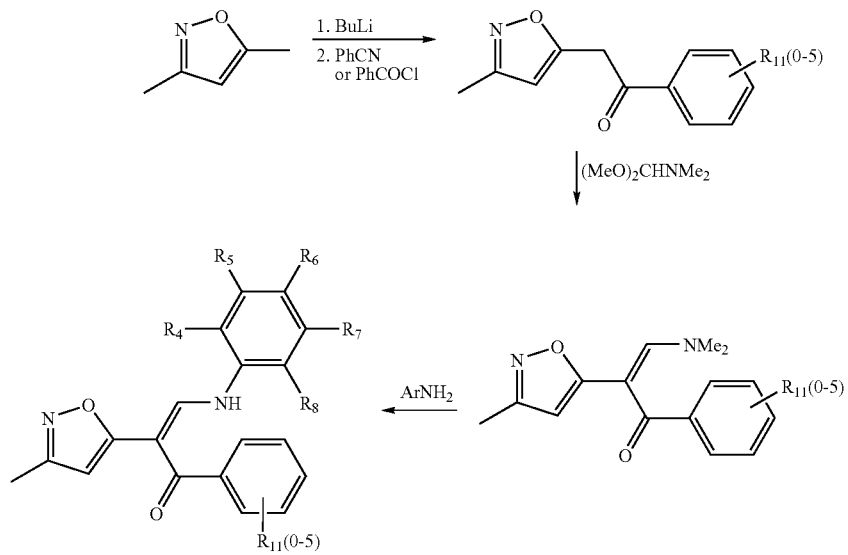

Scheme 2

The synthesis of compounds of Formula I (HET=tetrazole) was accomplished as in Scheme 3 starting with commercially available ethyl 1H-tetrazoleacetate (Aldrich).

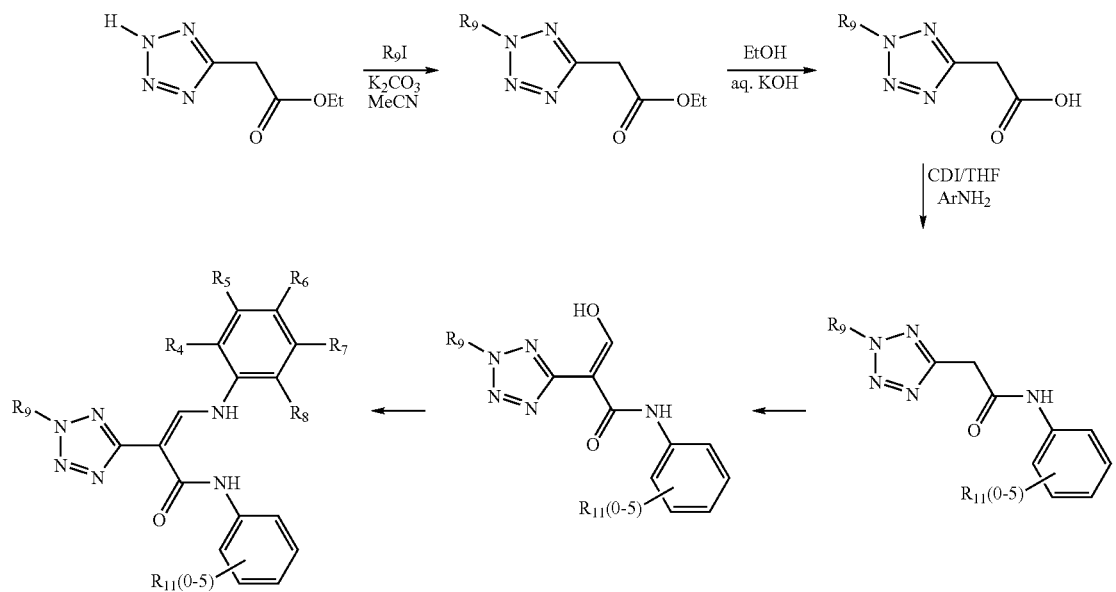

The synthesis of compounds of Formula V is given in Scheme 4.

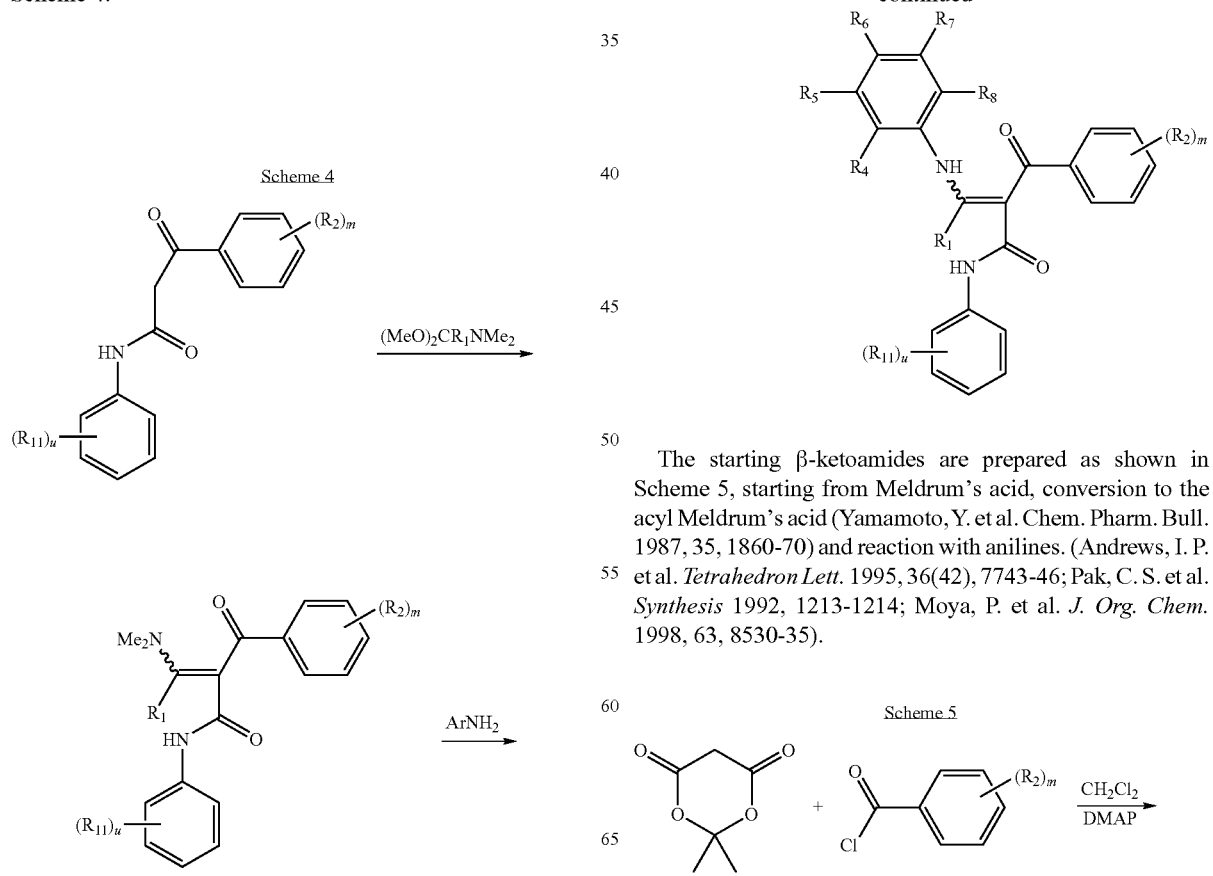

The starting β-ketoamides are prepared as shown in Scheme 5, starting from Meldrum's acid, conversion to the acyl Meldrum's acid (Yamamoto, Y. et al. *Chem. Pharm. Bull.* 1987, 35, 1860-70) and reaction with anilines. (Andrews, I. P. et al. *Tetrahedron Lett.* 1995, 36(42), 7743-46; Pak, C. S. et al. *Synthesis* 1992, 1213-1214; Moya, P. et al. *J. Org. Chem.* 1998, 63, 8530-35).

-continued

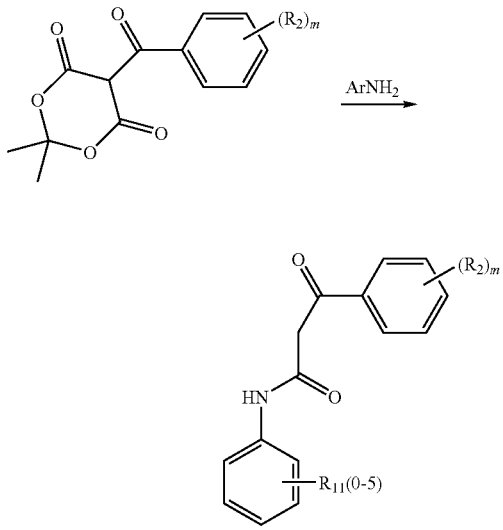

OOCYTE ELECTROPHYSIOLOGY: Individual compounds were tested for modulation of submaximal nicotine-evoked currents at α7 nAChRs using oocytes expressing human receptors. For each oocyte, the maximal nicotine-evoked currents were determined in response to 3 mM nicotine. All other currents were scaled to this value. The concentration of nicotine was adjusted to evoke a fractional current of approximately 0.05 (5% of max, or "$EC_5$"), and this concentration of nicotine was used to generate $EC_5$ control currents. Increasing concentrations of test compounds were applied to oocytes alone (pretreatment) and then in combination with the $EC_5$ concentration of nicotine (co-application). This protocol allowed measurement of both direct effects of test compounds on α7 nAChRs, and modulatory effects of compounds on nicotine-evoked responses. mRNA was prepared and stored using conventional techniques from cDNA clones encoding the human nicotinic receptor subunits. Preparation, micro-injection and maintenance of oocytes were performed as reported in detail previously (Whittemore et al., Mol. Pharmacol. 50: 1364-1375, 1996). Individual oocytes were injected with 5-50 ng of each subunit mRNA. For multiple subunit combinations, the mRNA ratios are: (1) α4β2 and α3β4 nAChRs (a 1:1 mixture); Following injections, oocytes were maintained at 16-17° C. in Barth's medium. Two-electrode voltage clamp recordings were made 3-14 days following mRNA injections at a holding voltage of −70 mV unless specified. The nicotinic recordings were done in $Ca^{++}$-free Ringer solution (mM: NaCl, 115; KCl, 2; $BaCl_2$, 1.8; HEPES, 5; pH 7.4) to limit $Ca^{++}$-activated chloride and muscarinic currents. Drug and wash solutions were applied using a microcapillary "linear array" (Hawkinson et al., Mol. Pharmacol. 49: 897-906, 1996) in order to allow rapid application of agonists. Currents were recorded on a chart recorder and/or PC-based computer for subsequent analysis. Test compounds were made up in DMSO over a concentration range of 0.001-10 mM and diluted 1000-3000-fold into the appropriate saline just prior to testing (final [DMSO]≦0.1%). The concentration-dependence of modulation was analyzed using GraphPad "Prism" curve-fitting software.

BEHAVIORAL: Mice were placed facing away from the door in the lit compartment of a 2 compartment activity chamber (Model E63-12, Coulbourn Instruments, Allentown, Pa.) with a guillotine door separating the lit from dark compartments. After 5 seconds, the guillotine door was raised and the entrance latency to the dark compartment (step-through latency) was recorded when the animal places all four paws in the dark compartment. After the animal spontaneously entered the dark compartment, the guillotine door was lowered and a 50 Hz square wave, 0.25 mA constant current shock was applied for 1.0 s. After 20-24 hours, the latency to enter the dark chamber was measured again. Various doses of test drug were administered 10 m before or immediately after the acquisition trial to measure drug effects on acquisition and consolidation respectively. The difference between test latency and acquisition latency was recorded and a significant (ANOVA, post-hoc Newman Keuls) increase in latency over controls suggests a positive effect on memory. The ability to restore disruption of acquisition and consolidation by the muscarinic antagonist scopolamine was also measured (Sarter et al., Psychopharmacologia 107: 144-159, 1992). Rotarod performance was measured as previously described to assess possible CNS depressant effects (Johnstone et al., Nat. Med. 10: 31-32, 2004).

EXAMPLE 1

α-[[(4-Ethoxyphenyl)amino]methylene]-β-oxo-N-phenylbenzenepropanamide a. α-[(Dimethylamino)methylene]-β-oxo-N-phenylbenzenepropanamide. A solution of 2-benzoylacetanilide (Aldrich; 1.088 g, 4.55 mmol) in 15 mL of $CH_2Cl_2$ was treated with neat N,N-dimethylformamide dimethyl acetal (0.75 mL, 670 mg, 5.63 mmol). The reaction was allowed to stir at rt overnight. Concentration in vacuo gave a solid that was adsorbed onto 3.3 g of silica gel and added to 17 cm of flash silica gel in a 5 cm dia. column. Elution with 2 L of 4:1 EtOAc/hexanes afforded 797 mg (61%) of the desired compound as a yellow solid. $^1$H NMR (400 MHz, $CDCl_3$) δ 10.70 (br s, 1H), 7.64 (d, 2H, J=8.1 Hz), 7.59 (d, 2H, J=7.3 Hz), 7.48 (t, 1H, J=6.8 Hz), 7.44 (s, 1H), 7.42 (t, 1H, J=7.0 Hz), 7.30 (t, 2H, J=8.0 Hz), 7.04 (t, 1H, J=7.3 Hz), 3.01 (br s, 6H).

b. α-[[(4-Ethoxyphenyl)amino]methylene]-β-oxo-N-phenylbenzenepropanamide. A solution of α-[(dimethylamino)methylene]-β-oxo-N-phenylbenzenepropanamide (109 mg, 0.37 mmol) in 2 mL of toluene was treated with neat p-phenetidine (47 µL, 50 mg, 0.36 mmol) added via syringe. The resulting solution was heated at reflux for 1 h. The reaction was allowed to cool to rt. The precipitate that formed was isolated by filtration and washed with toluene, affording 95 mg of the title compound as a yellow solid. $^1$H NMR (400 MHz, $CDCl_3$) δ 12.68 (d, 1H, J=13.0 Hz), 11.83 (s, 1H), 8.02 (d, 1H, J=13.0 Hz), 7.67 (d, 2H, J=8.2 Hz), 7.58-7.45 (m, 5H), 7.37 (t, 2H, J=8.0 Hz), 7.12 (t, 1H, J=7.4 Hz), 6.91 (d, 2H, J=9.0 Hz), 6.83 (d, 2H, J=9.0 Hz), 3.98 (q, 2H, J=7.0 Hz), 1.39 (t, 3H, J=7.0 Hz).

EXAMPLE 2

N-(4-Chlorophenyl)-α-[[(4-chlorophenyl)amino]methylene]-3-methyl-5-isoxazoleacetamide

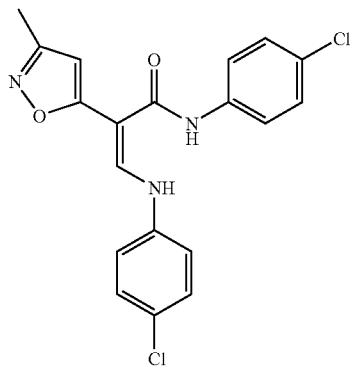

a. N-(4-Chlorophenyl)-3-methyl-5-isoxazoleacetamide. A suspension of 3-methyl-5-isoxazoleacetic acid (Aldrich; 3.72 g, 26.4 mmol) in 70 mL of $CH_2Cl_2$ was treated with neat oxalyl chloride (3.0 mL, 24 mmol). After stirring overnight at rt, the reaction was conc. in vacuo. The residue was dissolved in benzene and conc. to dryness. A solution of the acid chloride (2.57 g, 16.1 mmol) in 25 mL of $CH_2Cl_2$ was treated with 4-chloroaniline (2.06 g, 16.1 mmol). A solution of $Et_3N$ (2.5 mL, 18 mmol) in 20 mL of $CH_2Cl_2$ was added dropwise. After the addition was complete, the reaction was extracted with a 1 M aq. HCl solution. The organic layer was dried ($Na_2SO_4$), filtered and conc. in vacuo. The aqueous layer was made basic and extracted with EtOAc. The pooled EtOAc layers were washed with brine, dried ($Na_2SO_4$), filtered and conc. The solids obtained were combined and washed with $CH_2Cl_2$, affording 1.8 g of the amide as a solid.

b. N-(4-Chlorophenyl)-α-hydroxymethylene-3-methyl-5-isoxazoleacetamide. A suspension of 60% NaH in oil (Aldrich; 3.34 g, 83.5 mmol) in 100 mL of dry THF was treated with a solution of N-(4-chlorophenyl)-3-methyl-5-isoxazoleacetamide (7.05 g, 28.1 mmol) in 75 mL of THF added over 1 h. After stirring at rt for 15 m, neat ethyl formate (15 mL) was added dropwise via addition funnel over 30 mins. Gas evolution was observed and the reaction was cooled in an ice-water bath. When the gas evolution had moderated, the cold bath was removed and the reaction was allowed to stir at rt for 3 h. The reaction was recooled in an ice-water bath and quenched with water and a 1N HCl solution. The resulting mixture was washed with EtOAc (3×75 mL). The EtOAc layers were combined, washed with brine, dried ($Na_2SO_4$), filtered and conc. in vacuo. The solid was then triturated with hexanes, affording 7.4 g (90% yield) of the product as a pink solid.

c. N-(4-Chlorophenyl)-α-[[(4-chlorophenyl)amino]methylene]-3-methyl-5-isoxazoleacetamide. A suspension of N-(4-chlorophenyl)-α-hydroxymethylene-3-methyl-5-isoxazoleacetamide (7.27 g, 26.1 mmol) in 125 mL of EtOH was treated with a solution of 4-chloroaniline (3.32 g, 26.0 mmol) in 20 mL of EtOH. After 5 m, a solution formed and then a ppt formed. After stirring overnight, the solid was isolated by filtration and washed with EtOH. The light yellow solid obtained weighed 9.01 g (89% yield). $^1$H NMR (400 MHz, $CDCl_3$) δ 11.45 (d, 1H, J=12.5 Hz), 8.25 (s, 1H), 7.67 (d, 1H, J=12.5 Hz), 7.46 (d, 2H, J=8.8 Hz), 7.28 (d, 4H, J=8.8 Hz), 6.98 (d, 2H, J=8.8 Hz), 5.98 (s, 1H), 2.31 (s, 3H).

The following compounds were prepared by using the method described above for N-(4-chlorophenyl)-α-[[(4-chlorophenyl)amino]methylene]-3-methyl-5-isoxazoleacetamide:

3-Methyl-N-phenyl-5-isoxazoleacetamide: Yield 72% as a white solid, mp 115-116° C.; $^1$H NMR (400 MHz, $CDCl_3$) δ 7.55 (br s, 1H), 7.50 (d, 2H), 7.33 (m, 2H), 7.12 (t, 1H), 6.17 (s, 1H), 3.84 (s, 2H), 2.31(s, 3H). TOF MS ES+ m/z 217 (MH+).

N-(4-Fluorophenyl)-3-methyl-5-isoxazoleacetamide: Spectroscopic data of compound is consistent with structure.

EXAMPLE 3

α-[[(4-Ethoxyphenyl)amino]methylene]-3-methyl-N-phenyl-5-isoxazoleacetamide

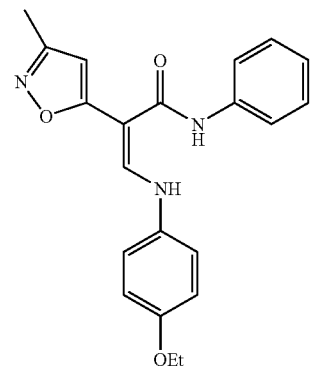

A solution of 3-methyl-N-phenyl-5-isoxazoleacetamide (10 mmol) and N,N-dimethyl-formamide dimethyl acetal (1.80 g, 2.0 mL, 15 mmol) in 20 mL of toluene was stirred at 80° C. for 24 h. The reaction was conc. to dryness. The residue was dissolved in 5 mL of toluene and treated with neat p-phenetidine (10 mmol). After heating at reflux for 2 h, the reaction was evaporated to dryness. Purification by column chromatography (2% MeOH/$CH_2Cl_2$) afforded the title compound as a light yellow solid, mp 114-115° C.

$^1$H NMR (400 MHz, $CDCl_3$): δ 11.40 (d, 1H), 8.25 (b, 1H), 7.70 (d, 1H), 7.54 (d, 2H), 7.35 (m, 2H), 7.14 (t, 1H), 7.00 (d, 2H), 6.90 (d, 2H), 5.96 (s, 1H), 4.00 (q, 2H), 2.36 (s, 3H), 1.40 (t, 3H); TOF MS ES+ m/z 364 (MH+).

The following compounds were prepared by using the method described above for α-[[(4-ethoxyphenyl)amino]methylene]-3-methyl-N-phenyl-5-isoxazoleacetamide:

α-[[(4-Iodophenyl)amino]methylene]-3-methyl-N-phenyl-5-isoxazoleacetamide: Yield 25% as a light yellow solid, mp 128-130° C.; $^1$H NMR (400 MHz, $CDCl_3$): δ 11.50 (d, 1H), 8.22 (br s, 1H), 7.73 (d, 1H), 7.64 (d, 2H), 7.50 (d, 2H), 7.36 (t, 2H), 7.15 (q, 1H), 6.83 (d, 2H), 5.98 (s, 1H), 2.30(s, 3H); TOF MS ES+ m/z 446 (MH+).

α-[[(4-Chlorophenyl)amino]methylene]-3-methyl-N-phenyl-5-isoxazoleacetamide: Purified by recrystallization from MeOH (40% yield) as a white solid, mp 153-155° C.; $^1$H NMR (400 MHz, $CDCl_3$): δ 11.50 (d, 1H), 8.23 (br s, 1H), 7.72 (d, 1H), 7.55 (m, 1H), 7.54 (d, 2H), 7.35 (m, 2H), 7.32 (d, 2H), 7.15 (t, 1H), 7.00 (d, 2H), 5.98 (s, 1H), 2.30 (s, 3H); TOF MS ES+ m/z 354 (MH+).

α-[[(4-Ethoxyphenyl)amino]methylene]-3-methyl-N-(2-pyridyl)-5-isoxazoleacetamide: Purified by recrystallization from MeOH (20% yield) as a white solid, mp 129-130° C.; $^1$H NMR (400 MHz, $CDCl_3$): δ 11.30 (d, 1H), 8.50 (br s, 1H), 8.35 (d, 1H), 8.25 (d, 1H), 8.20 (d, 1H), 7.70 (m, 1H), 7.10 (m, 1H), 7.05 (d, 2H), 6.90 (d, 2H), 6.00 (s,1H), 4.00 (q, 2H), 2.30 (s, 3H), 1.35 (t, 3H); TOF MS ES+ m/z 365(MH$^+$).

N-(4-Ethoxyphenyl)-α-[[(4-ethoxyphenyl)amino]methylene]-3-methyl-5-isoxazole-acetamide: Spectroscopic data of compound is consistent with structure.

α-[[(4-Ethoxyphenyl)amino]methylene]-3-methyl-N-[4-(trifluoromethyl)phenyl]-5-isoxazoleacetamide: Spectroscopic data of compound is consistent with structure.

N-(4-Chlorophenyl)-α-[[(4-ethoxyphenyl)amino]methylene]-3-methyl-5-isoxazoleacetamide; $^1$H NMR (400 MHz, CDCl$_3$) δ 11.42 (d, 1H, J=12.7 Hz), 8.30 (br s, 1H), 7.69 (d, 1H, J=12.8 Hz), 7.49 (d, 2H, J=9.0 Hz), 7.30 (d, 2H, J=8.9 Hz), 7.01 (d, 2H, J=9.0 Hz), 6.88 (d, 2H, J=9.0 Hz), 5.96 (s, 1H), 4.01 (q, 2H, J=7.0 Hz), 2.32 (s, 3H), 1.41 (t, 2H, J=7.0 Hz).

α-[[(4-Ethoxyphenyl)amino]methylene]-N-(4-ethynylphenyl)-3-methyl-5-isoxazole-acetamide;

N-(3-Chlorophenyl)-α-[[(4-chlorophenyl)amino]methylene]-3-methyl-5-isoxazole-acetamide; $^1$H NMR (400 MHz, CDCl$_3$) δ 11.49 (d, 1H, J=12.3 Hz), 8.28 (br s, 1H), 7.71 (d, 1H, J=12.5 Hz), 7.70 (s, 1H), 7.36-7.25 (m, 4H), 7.12 (d, 1H, J=7.9 Hz), 7.02 (d, 2H, J=8.1 Hz), 6.01 (s, 1H), 2.34 (s, 3H).

N-(2-Chlorophenyl)-α-[[(4-chlorophenyl)amino]methylene]-3-methyl-5-isoxazole-acetamide: $^1$H NMR (400 MHz, CDCl$_3$) δ 11.45 (d, 1H, J=12.5 Hz), 8.72 (br s, 1H), 8.38 (d, 1H, J=8.3 Hz), 7.77 (d, 1H, J=12.7 Hz), 7.40 (d, 1H, J=9.1 Hz), 7.32 (d, 2H, J=8.7 Hz), 7.25 (m, 1H), 7.04 (m, 1H), 7.03 (d, 2H, J=8.9 Hz), 6.13 (s, 1H), 2.35 (s, 3H); and N-(4-Chlorophenyl)-α-[[(3-chlorophenyl)amino]methylene]-3-methyl-5-isoxazole-acetamide.

EXAMPLE 4

N-(4-Chlorophenyl)-α-[[(3-fluorophenyl)amino]methylene]-3-methyl-5-isoxazole-acetamide A solution of N-(4-chlorophenyl)-3-methyl-5-isoxazoleacetamide (4.0 mmol) in THF (20 mL) was slowly added into a suspension of NaH (60%, 0.40 g, 10 mmol) in 10 mL of THF. The reaction mixture was stirred at rt for 30 mins. and neat ethyl formate (1.6 mL, 20 mmol) was added. After stirring at rt overnight, the solvent was removed under reduced pressure and the crude product was partitioned between EtOAc and a 1N aqueous NaOH solution. The aqueous solution was separated, acidified with an aqueous 1N HCl solution, and extracted with EtOAc. The EtOAc layers were dried over Na$_2$SO$_4$, filtered and conc. The crude hydroxymethylene intermediate was carried on without purification. Reaction with 3-fluoroaniline in CH$_2$Cl$_2$ at rt for 1 h afforded the title compound after removal of the solvent in vacuo and two recrystallizations from MeOH, yield 44%. $^1$H NMR (400 MHz, CDCl$_3$) δ 11.50 (d, 1H), 8.15, 8.30 (d, 1H), 7.70 (d, 1H), 7.50 (d, 2H), 7.30 (dd, 3H), 6.80 (m, 3H), 6.02, 6.22 (s,1H), 2.30, 2.35 (s, 3H); TOF MS ES+ m/z 372, 374 (MH$^+$); 394, 396 (M+Na$^+$).

The following compounds were prepared by using the method described above for N-(4-chlorophenyl)-α-[[(3-fluorophenyl)amino]methylene]-3-methyl-5-isoxazoleacetamide: N-(4-Chlorophenyl)-α-[[(4-hydroxyphenyl)amino]methylene]-3-methyl-5-isoxazoleacetamide: Reaction with p-aminophenol was carried out in DMSO at rt for 24 h; TOF MS ES m/z 392 (M+Na$^+$);

N-(4-Chlorophenyl)-α-[[(4-fluorophenyl)amino]methylene]-3-methyl-5-isoxazoleacetamide; Yield 54%; $^1$H NMR (400 MHz, CDCl$_3$) δ 11.50 (d, 1H), 8.28 (s, 1H), 7.70 (d, 1H), 7.50 (d, 2H), 7.30 (d, 4H), 7.00 (d, 2H), 6.02, 6.22 (s, 1H), 2.30, 2.35 (s, 3H); TOF MS ES+ m/z 372, 374 (MH$^+$), 394, 396(M+Na$^+$);

N-(4-Fluorophenyl)-α-[[(4-hydroxyphenyl)amino]methylene]-3-methyl-5-isoxazole-acetamide; Yield 40%. α-[[(4-Chlorophenyl)amino]methylene]-N-(4-fluorophenyl)-3-methyl-5-isoxazoleacetamide: Yield 44%, $^1$H NMR (400 MHz, CDCl$_3$) δ 11.50 (d, 1H), 8.28 (s, 1H), 7.70 (d, 1H), 7.50 (d, 2H), 7.30 (d, 4H), 7.00 (d, 2H), 6.01, 6.20 (s, 1H), 2.30, 2.35 (s, 3H); TOF MS ES+ m/z 372, 374 (MH$^+$); 394, 396 (M+Na$^+$); α-[[(4-Ethoxyphenyl)amino]methylene]-N-(4-fluorophenyl)-3-methyl-5-isoxazoleacetamide: Yield 47%; $^1$H NMR (400 MHz, CDCl$_3$) δ 11.40 (d, 1H, J=12.3 Hz), 8.26 (br s, 1H), 7.67 (d, 1H, J=12.9 Hz), 7.48 (d, 2H, J=9.1 Hz), 7.04 (d, 2H, J=8.9 Hz), 7.01 (d, 2H, J=8.9 Hz), 6.98 (d, 2H, J=8.9 Hz), 5.95 (s, 1H), 4.00 (q, 2H, J=6.9 Hz), 2.31 (s, 3H), 1.40 (t, 2H, J=6.9 Hz); N-(4-Chlorophenyl)-α-[(3-fluorophenylamino)methylene]-3-methyl-5-isoxazole-acetamide; Isolated in 44% yield. $^1$H NMR (400 MHz, CDCl$_3$) δ 11.50 (d, 1H), 8.30, 8.15 (d, 1H), 7.70 (d, 1H), 7.50 (d, 2H), 7.30 (dd, 3H), 6.80 (m, 3H), 6.22, 6.02 (s, 1H), 2.35, 2.30 (s, 3H). TOF MS ES+ m/z 372, 374 (M+H$^+$) 394, 396 (M+Na$^+$).

N-(4-Chlorophenyl)-α-[(1H-indol-5-ylamino)methlene]-3-methyl-5-isoxazoleacetamide; Isolated as an yellow solid, yield 25%. $^1$H NMR (400 MHz, CDCl$_3$) δ 11.50 (d, 1H), 8.30 (s, 1H), 8.24 (d,1H), 8.20 (s, 1H), 7.80 (d, 1H), 7.49 (d, 2H), 7.32 (d, 2H), 7.28 (d, 2H), 6.95 (d, 1H), 6.50 (s, 1H), 5.94 (s, 1H), 2.33 (s, 3H). TOF MS ES+ m/z 394, 396 (M+H$^+$), 416, 418 (M+Na$^+$).

N-(4-Chlorophenyl)-α-[(3-hydroxylphenylamino)methylene]-3-methyl-5-isoxazoleacetamide: Prepared as described for the 4-hydroxy isomer but starting with 3-aminophenol in 41% yield. $^1$H NMR (400 MHz, DMSO-d$_6$) δ 10.60 (d, 1H), 9.50 (s, 1H), 9.33 (s, 1H), 7.80 (d, 1H), 7.62 (d, 2H), 7.32 (d, 2H), 7.07 (dd, 1H), 6.69 (d, 1H), 6.62 (s, 1H), 6.44 (d, 1H), 6.33 (s, 1H), 2.19 (s, 3H). MS ES+ m/z 370, 372 (M+H$^+$), 392, 394 (M+Na$^+$).

N-(4-Chlorophenyl)-α-[(isoquinolin-5-ylamino)methylene]-3-methyl-5-isoxazole-acetamide; Isolated as a yellow solid, yield 76%. $^1$H NMR (400 MHz, CDCl$_3$) δ 12.33 (d, 1H), 9.24 (s,1H), 8.60 (d,1H), 8.33 (s, 1H), 7.88 (d, 1H), 7.72 (d, 1H), 7.70 (d, 1H), 7.58 (d, 1H), 7.54 (d, 2H), 7.40 (d, 1H), 7.30 (d, 2H), 6.00 (s, 1H), 2.33 (s, 3H). TOF MS ES+ m/z 405, 407 (M+H$^+$), 427, 429 (M+Na$^+$).

N-(4-Chlorophenyl)-α-[(indazol-6-ylamino)methylene]-3-methyl-5-isoxazoleacetamide: Isolated as a yellow solid, yield 50%. $^1$H NMR (400 MHz, DMSO-d$_6$) δ 12.90 (s, 1H), 10.80 (d, 1H), 9.38 (s, 1H), 8.00 (d, 1H), 7.95 (s, 1H), 7.67 (d, 2H), 7.38 (s, 1H), 7.30 (d, 2H), 7.10 (d, 1H), 6.40 (s, 1H), 2.24 (s, 3H). TOF MS ES+ m/z 394, 396 (M+H$^+$), 416, 418 (M+Na$^+$).

N-(4-Chlorophenyl)-α-[(indazol-5-ylamino)methylene]-3-methyl-5-isoxazoleacetamide: Isolated as a yellow solid. $^1$H NMR (400 MHz, DMSO-d$_6$) δ 13.00 (s, 1H), 10.86 (d, 1H), 9.27 (s, 1H), 7.98 (d, 1H), 7.95-7.30 (m, 8H), 6.34 (s, 1H), 2.24 (s, 3H). TOF MS ES+ m/z 394, 396 (M+H$^+$), 416, 418 (M+Na$^+$).

N-(4-Chlorophenyl)-α-[(3-methylisoxazol-5-ylamino)methylene]-3-methyl-5-isoxazoleacetamide: Isolated as a colorless solid in 40% yield. $^1$H NMR (400 MHz, CDCl$_3$) δ 11.87 (d, 1H), 8.39 (s, 1H), 7.65 (d, 1H), 7.45 (d, 2H), 7.28 (d, 2H), 6.08 (s, 1H), 5.38 (s, 1H), 2.34 (s, 3H), 2.24 (s, 3H). TOF MS ES+ m/z 359, 361 (M+H$^+$), 381, 383 (M+Na$^+$).

N-(4-Chlorophenyl)-3-methyl-α-[(5-methylisoxazol-3-ylamino)methylene]-5-isoxazoleacetamide; Isolated as a brown solid in 35% yield. $^1$H NMR (400 MHz, CDCl$_3$) δ 11.20 (d, 1H), 8.40 (s, 1H), 7.85 (d, 1H), 7.45 (d, 2H), 7.28 (d, 2H), 6.05 (s, 1H), 5.76 (s, 1H), 2.35(s, 3H), 2.31 (s, 3H). TOF MS ES+ m/z 359, 361 (M+H$^+$), 381, 383 (M+Na$^+$).

N-(4-Fluorophenyl)-3-methyl-α-[(5-methylisoxazol-3-ylamino)methylene]-5-isoxazoleacetamide; $^1$H NMR (400 MHz, CDCl$_3$) δ 11.22 (d, 1H, J=11.9 Hz), 8.40 (s, 1H), 7.87

(d, 1H, J=12.2 Hz), 7.48 (m, 2H), 7.05 (t, 2H, J=8.5 Hz), 6.08 (s, 1H), 5.78 (s, 1H), 2.39 (s, 3H), 2,33 (s, 3H).

N-(4-Chlorophenyl)-3-methyl-α-[(4-nitrophenylamino)methylene]-5-isoxazoleacetamide: Isolated as a yellow solid, yield 50%. ¹H NMR (400 MHz, CDCl₃) δ 11.76 (d, 1H), 8.25 (s, 1H), 8.23 (d, 2H), 7.73 (d, 1H), 7.46 (d, 2H), 7.30 (d, 2H), 7.10 (d, 2H), 6.09 (s, 1H), 2.32 (s, 3H). TOF MS ES+ m/z 399, 401 (M+H⁺), 421, 423 (M+Na⁺).

N-(4-Chlorophenyl)-α-[[(4-dimethylamino)phenylamino]methylene]-3-methyl-5-isoxazoleacetamide; Isolated as a yellow-green solid in 25% yield. ¹H NMR (400 MHz, CDCl₃) δ 11.50 (d, 1H), 8.30 (s, 1H), 7.70 (d, 1H), 7.49 (d, 2H), 7.30 (d, 2H), 7.05 (d, 2H), 6.75 (d, 2H), 5.96 (s, 1H), 3.00 (s, 6H), 2.33 (s, 3H). TOF MS ES+ m/z 397, 399 (M+H⁺), 419, 421 (M+Na⁺)

α-[(3-Azabicyclo[3.3.0]octyl-3-amino)methylene]-N-(4-chlorophenyl)-3-methyl-5-isoxazoleacetamide: Isolated as a white solid in 20% yield. ¹H NMR (400 MHz, CDCl₃) δ 9.89 (d, 1H), 8.36 (s,1H), 7.68 (d, 1H), 7.41 (d, 2H), 7.23 (d, 2H), 5.86 (s, 1H), 2.65 (d, 4H), 2.24 (s, 3H), 1.70 (m, 4H), 1.55 (m, 2H), 1.43 (m, 2H). TOF MS ES+ m/z 387, 389 (M+H⁺), 409, 411 (M+Na⁺).

N-(4-Fluorophenyl)-α-[(4-fluorophenylamino)methylene]-3-methyl-5-isoxazoleacetamide: ¹H NMR (400 MHz, CDCl₃) δ 11.24 (d, 1H, J=9.0 Hz), 8.24 (s, 1H), 7.69 (d, 1H, J=9.0 Hz), 7.49-7.46 (m, 2H), 7.08-7.04 (m, 6H), 6.00 (s, 1H), 2.40 (s, 3H). TOF MS ES+ m/z 356 (M+H⁺), 378 (M+Na⁺).

α-[(4-Ethylphenylamino)methylene]-N-(4-fluorophenyl)-3-methyl-5-isoxazoleacetamide; ¹H NMR (400 MHz, CDCl₃) δ 11.40 (d, 1H, J=9.0 Hz), 8.23 (s, 1H), 7.73 (d, 1H, J=9.0 Hz), 7.46-7.43 (m, 2H), 7.15 (d, 2H, J=6.0 Hz), 7.04-6.96 (m, 4H), 6.95 (s, 1H), 2.59 (q, 2H, J=6.0 Hz), 2.32 (s, 3H) 1.19 (t, 3H, J=6.0 Hz). TOF MS ES+ m/z 365 (M+H⁺), 368 (M+Na⁺).

N-(4-Fluorophenyl)-3-methyl-α-[(4-methylphenylamino)methylene]-5-isoxazoleacetamide: ¹H NMR (400 MHz, CDCl₃) δ 11.40 (d, 1H, J=9.0 Hz), 8.23 (s, 1H), 7.72 (d, 1H, J=9.0 Hz), 7.46-7.43 (m, 2H), 7.12 (d, 2H, J=6.0 Hz), 7.01 (t, 2H, J=6.0 Hz), 6.95 (d, 2H, J=6.0 Hz), 5.95 (s, 1H), 2.30 (s, 3H). TOF MS ES+ m/z 374 (M+Na⁺).

EXAMPLE 5

N-(4-Chlorophenyl)-α-[(4-ethoxyphenyl)amino]methylene]-2-pyridineacetamide

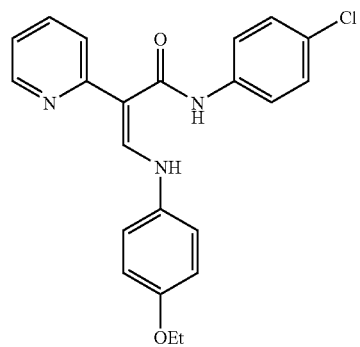

a. N-(4-Chlorophenyl)-2-pyridineacetamide. A suspension of 2-pyridineacetic acid hydrochloride (Aldrich; 1.74 g, 10 mmol) and carbonyl diimidazole (1.95 g, 12 mmol) in anhydrous THF (20 mL) was stirred at rt for 1 h. To the mixture was added solid 4-chloroaniline (1.28 g, 10 mmol). After stirring overnight, the solvent was removed and the residue was partitioned between water and EtOAc. The organic layer was dried over Na₂SO₄ and evaporated to dryness. The crude product was recrystallized from 20 mL of toluene affording 1.5 g (60%) of the amide as a solid. TOF MS ES+ m/z 247 (MH⁺), 269 (M+Na⁺).

b. N-(4-Chlorophenyl)-α-hydroxymethylene-2-pyridineacetamide. A solution of N-(4-chlorophenyl)-2-pyridineacetamide (0.50 g, 2.0 mmol) in THF (10 mL) was slowly added to a suspension of NaH (60% in oil; 0.15 g, 4.0 mmol) in THF (10 mL). The mixture was stirred at rt for 30 mins. and neat ethyl formate (0.80 mL, 10 mmol) was added. After stirring overnight, the precipitate that had formed was collected and washed with EtOAc. Recrystallization from MeOH afforded 0.60 g (55%) of the product as an off-white solid. TOF MS ES+ m/z 275 (MH⁺), 297 (M+Na⁺).

c. N-(4-Chlorophenyl)-α-[(4-ethoxyphenyl)amino]methylene]-2-pyridineacetamide. A solution of N-(4-chlorophenyl)-α-hydroxymethylene-2-pyridineacetamide (55 mg, 0.20 mmol) and p-phenetidine (27 μL, 0.22 mmol) were refluxed in toluene (3 mL) for 24 h. The mixture was evaporated to dryness. Purification by column chromatography with 1:1 EtOAc/hexanes, followed by recrystallization from MeOH, gave 18 mg (25%) of the title compound as a light yellow solid. ¹H NMR (CDCl₃, 400 MHz) δ 12.70 (s, 1H), 11.70 (d, 1H), 8.50 (d, 1H), 7.70 (d, 1H), 7.65 (m, 1H), 7.60 (d, 2H), 7.30 (d, 1H), 7.25 (d, 2H), 7.05 (m, 1H), 7.00 (d, 2H), 6.85 (d, 2H), 4.00 (t, 2H), 1.40 (t, 3H). TOF MS ES+ m/z 394 (MH⁺), 416 (M+Na⁺).

The following compounds were prepared by using the procedure described above for N-(4-chlorophenyl)-α-[(4-ethoxyphenyl)amino]methylene]-2-pyridineacetamide:

N-(4-Chlorophenyl)-α-[(4-chlorophenyl)amino]methylene]-2-pyridineacetamide: 10% yield from N-(4-chlorophenyl)-α-hydroxymethylene-2-pyridineacetamide. ¹H NMR (CDCl₃, 400 MHz) δ 12.70 (s, 1H), 11.70 (d, 1H), 8.50 (d, 1H), 7.72 (d, 1H), 7.68 (m, 1H), 7.58 (d, 2H), 7.36 (d, 1H), 7.28 (dd, 4H), 7.10 (m, 1H), 7.00 (d, 2H). TOF MS ES+ m/z 384, 386 (MH⁺), 406, 408 (M+Na⁺).

EXAMPLE 4

1-(2-Chlorophenyl)-3-[(4-ethoxyphenyl)amino]2-(2-pyridinyl)-2-propen-1-one

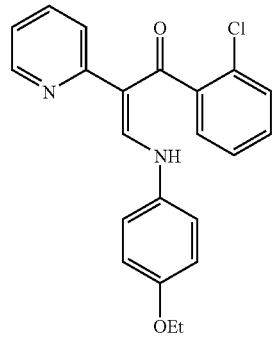

a. 1-(2-Chlorophenyl)-2-(2-pyridinyl)ethanone. To a solution of 2-pyridineacetic acid hydrochloride (1.74 g, 10 mmol) in THF (20 mL) was slowly added 20 mL of a 1.6 M (32 mmol) butyllithium solution in hexanes at −70° C. After the addition was complete the reaction was stirred cold for 30 m, and then 1.3 mL (10 mmol) of 2-chlorobenzoyl chloride was added. The mixture was stirred cold for 1 h and then allowed to warm to rt. After stirring overnight, the reaction was poured into a separatory funnel containing 50 mL of water and 1 mL of an aq. 1N HCl solution. The organic layer was separated and the aqueous layer was extracted with EtOAc. The combined organic phases were washed with two portions of a saturated aqueous solution of sodium bicarbonate, followed by water, and dried over $Na_2SO_4$. Removal of the solvent under reduced pressure gave 2.0 g (90%) of crude product. Purification by chromatography with 1:1 EtOAc/hexanes afforded 0.60 g (25%) of the product as an oil. TOF MS ES+ m/z 232, 234 ($MH^+$), 254, 256 ($M+Na^+$).

b. 1-(2-Chlorophenyl)-3-[(4-ethoxyphenyl)amino]-2-(2-pyridinyl)-2-propen-1-one. 1-(2-Chlorophenyl)-2-(2-pyridinyl)ethanone (93 mg, 0.40 mmol) and N,N-dimethylformamide dimethyl acetal (0.26 mL, 2.0 mmol) were heated in toluene (3 mL) at 80° C. for 2 h. The resulting mixture was evaporated to dryness under reduced pressure at 80° C. The residue was dissolved in 3 mL of toluene and neat p-phenetidine (56 µL, 0.40 mmol) was added and the mixture was refluxed for 2 h. The solvent was then removed in vacuo and the residue was purified by column chromatography with 1:1 EtOAc/hexanes. Recrystallization of the crude product from MeOH gave 52 mg (50%) of the title compound as a light yellow solid. $^1$H NMR (400 MHz, $CDCl_3$) δ 13.40 (d, 1H), 8.80 (d, 1H), 7.80-6.82 (m, 12H), 4.00 (q, 2H), 1.40 (t, 3H). TOF MS ES+ m/z 379, 381 ($MH^+$), 401, 403 ($M+Na^+$).

The following compounds were prepared by using the procedure described above for 1-(2-chlorophenyl)-3-[(4-ethoxyphenyl)amino]-2-(2-pyridinyl)-2-propen-1-one:

1-(2-Chlorophenyl)-3-[(4-chlorophenyl)amino]-2-(2-pyridinyl)-2-propen-1-one. $^1$H NMR (400 MHz, $CDCl_3$) δ 13.40 (d, 1H), 8.80 (d, 1H), 8.60-6.82 (m, 12H). TOF MS ES+ m/z 369, 371 ($MH^+$), 391, 393 ($M+Na^+$).

3-[(4-Ethoxyphenyl)amino]-1-phenyl-2-(2-pyridinyl)-2-propen-1-one. $^1$H NMR (400 MHz, $CDCl_3$) δ 13.15 (d, 1H), 8.60 (d, 1H), 8.40-6.80 (m, 13H), 4.00 (q, 2H), 1.40 (t, 3H). TOF MS ES+ m/z 345, 346 ($MH^+$), 367, 368 ($M+Na^+$).

3-[(4-Chlorophenyl)amino]-1-phenyl-2-(2-pyridinyl)-2-propen-1-one. $^1$H NMR (400 MHz, $CDCl_3$) δ 13.20 (d, 1H), 8.60 (d, 1H), 8.30-6.80 (m, 13H). TOF MS ES+ m/z 335, 337 ($MH^+$), 357, 359 ($M+Na^+$).

3-[(4-Hydroxyphenyl)amino]-1-phenyl-2-(2-pyridinyl)-2-propen-1-one. $^1$H NMR (400 MHz, $CDCl_3$) δ TOF MS ES+ m/z 317 ($MH^+$), 339 ($M+Na^+$).

1-(2-Fluorophenyl)-2-(2-pyridinyl)ethanone. TOF MS ES+ m/z 216 ($MH^+$), 238 ($M+Na^+$).

EXAMPLE 5

3-[(4-Hydroxyphenyl)amino]-2-(3-methyl-5-isoxazolyl)-1-phenyl-2-propen-1-one

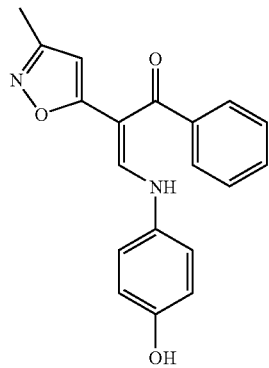

a. 2-(3-Methyl-5-isoxazolyl)-1-phenyl-1-ethanone. To a solution of 8.73 g (90 mmol) of 3,5-dimethylisoxazole in 100 mL of THF at −70° C. under $N_2$ was added dropwise a 1.55 M solution of nBuLi in hexanes (56.4 mL, 87 mmol). After stirring cold for 30 m, a solution of 10.3 g (100 mmol) of benzonitrile in 50 mL of THF was added dropwise. The reaction was allowed to warm to rt and stirred overnight. The solvent was removed in vacuo and the residue was partitioned between EtOAc and water. The organic layer was separated, washed with an aq. 1N HCl solution, dried ($Na_2SO_4$), filtered and conc. to dryness. Purification by silica gel chromatography (1:1 EtOAc/hexanes) followed by recrystallization gave the desired product as colorless crystals, mp 75-77° C. (25% yield; lit, Hicks, M. J. and Tong, Y. C., U.S. Pat. No. 5,338,856, Aug. 16, 1994, mp 73-74° C.). $^1$H NMR ($CDCl_3$, 400 MHz) δ 8.00 (d, 2H), 7.60 (m, 1H), 7.50 (d, 2H), 6.15 (s, 1H), 4.40 (s, 2H), 2.30 (s, 3H); TOF MS ES+ m/z 202 ($MH^+$).

b. 3-[(4-Hydroxyphenyl)amino]-2-(3-methyl-5-isoxazolyl)-1-phenyl-2-propen-1-one. A solution of 2-(3-methyl-5-isoxazolyl)-1-phenyl-1-ethanone (200 mg, 1.0 mmol) in 10 mL of toluene was treated with N,N-dimethylformamide dimethyl acetal (0.26 g, 2.0 mmol) and heated at 80° C. overnight. The reaction was conc. to dryness. The residue was dissolved in toluene (10 mL) and 110 mg (1.0 mmol) of p-aminophenol and 150 µL of triethylamine were added. After 2 hrs at reflux, the reaction was allowed to cool to rt. The crystals that formed were isolated by filtration and washed with toluene, affording a 70% yield of the title compound as a yellow solid. $^1$H NMR ($CDCl_3$, 400 MHz; 1:1 mixture of isomers) δ 12.50 (d, 1H), 8.10 (d, 1H), 7.45 (d, 2H), 7.40 (m, 1H), 7.35 (d, 2H), 7.10 (d, 2H), 6.95 (d, 2H), 6.20 (s, 1H), 5.10 (s, 1H), 2.18 (s, 3H).

The following compounds were prepared by using the method described for 3-[(4-hydroxyphenyl)amino]-2-(3-methyl-5-isoxazolyl)-1-phenyl-2-propen-1-one.

3-[(4-Ethoxyphenyl)amino]-2-(3-methyl-5-isoxazolyl)-1-phenyl-2-propen-1-one. Yellow solid, mp 162-164° C.; $^1$H NMR ($CDCl_3$, 400 MHz; 1:1 mixture of isomers) δ 12.49 (d, 1H, J=12.8 Hz), 9.12 (d, 1H, J=14.0 Hz), 8.04 (d, 1H, J=13.1 Hz), 7.73 (d, 1H, J=14.0 Hz), 7.61-7.35 (m, 6H), 7.15 (d, 2H, J=9.2 Hz), 5.16 (s, 1H), 4.04 (q, 2H, J=7.0 Hz), 3.99 (q, 2H, J=7.0 Hz), 2.37 (s, 3H), 2.14 (s, 3H), 1.43 (t, 3H, J=7.0 Hz), 1.40 (t, 3H, J=7.0 Hz).

3-[(4-Chlorophenyl)amino]-2-(3-methyl-5-isoxazolyl)-1-phenyl-2-propen-1-one. Off-white solid, mp 163-164° C. TOF MS ES+ m/z 339 ($MH^+$).

EXAMPLE 6

1-(2-Chlorophenyl)-3-[(4-ethoxyphenyl)amino]-2-(3-methyl-5-isoxazolyl)-2-propen-1-one

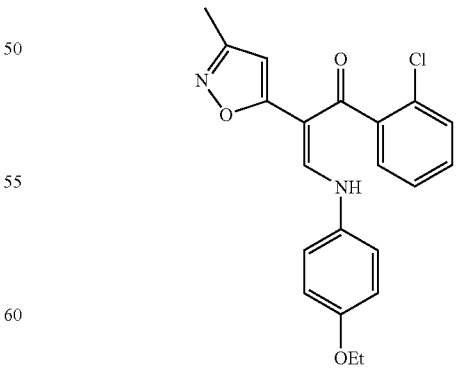

a. 1-(2-Chlorophenyl)-2-(3-methyl-5-isoxazolyl)-1-ethanone. To a solution of 1.41 g (10 mmol) of 3-methyl-5-isoxazoleacetic acid in 20 mL of THF at −70° C. under nitrogen was added dropwise 13 mL (20 mmol) of a 1.55 M solution of nBuLi in hexanes. After the addition was complete, the mixture was stirred cold for 30 mins. and then treated dropwise with a solution of 1.0 mL (7.90 mmol) of 2-chlorobenzoyl chloride in 20 mL of THF. During the addition the temperature was maintained at −60° C. After the addition was complete, the cold bath was removed and the reaction was stirred for 10 mins. The mixture was poured into a separatory funnel containing 30 mL of an aqueous 1 N HCl solution. The aqueous phase was extracted with EtOAc, the combined organic layers were washed with a sat. aqueous solution of NaHCO$_3$ and water, and then dried over Na$_2$SO$_4$. Removal of the solvent, purification by chromatography with EtOAc/hexane (1:1), followed by crystallization gave 0.2 g of 1-(2-chlorophenyl)-2-(3-methyl-5-isoxazolyl)-1-ethanone as colorless needles. $^1$H NMR (CDCl$_3$, 400 MHz) δ 7.58-7.34 (m, 5H), 6.15 (s, 1H), 4.40 (s, 2H), 2.30 (s, 3H); TOF MS ES+ m/z 236 (MH$^+$).

b. 1-(2-Chlorophenyl)-3-[(4-ethoxyphenyl)amino]-2-(3-methyl-5-isoxazolyl)-2-propen-1-one. A solution of 1-(2-chlorophenyl)-2-(3-methyl-5-isoxazolyl)-1-ethanone (0.10 g, 0.40 mmol) in 10 mL of toluene was treated with neat N,N-dimethylformamide dimethyl acetal (0.23 g, 1.0 mmol) and the mixture was heated at 80° C. overnight. The reaction was then conc. in vacuo. The residue was dissolved in 5 mL of toluene and p-phenetidine (55 mg, 0.4 mmol) was added and the mixture was heated under reflux for 2 h. Removal of solvent and crystallization of the residue from MeOH gave 130 mg of the title compound. TOF MS ES+ m/z 405 (M+Na$^+$).

The following compounds were prepared by using the method described for 1-(2-chlorophenyl)-3-[(4-ethoxyphenyl)amino]-2-(3-methyl-5-isoxazolyl)-2-propen-1-one.

1-(4-Chlorophenyl)-3-[(4-ethynylphenyl)amino]-2-(3-methyl-5-isoxazolyl)-2-propen-1-one: $^1$H NMR (400 MHz, CDCl$_3$), δ 12.30 (d, 1H), 8.05 (d, 1H), 7.60 (d, 2H), 7.40 (d, 2H), 7.30 (d, 2H), 5.40 (s, 1H), 3.20 (s, 1H), 2.20 (s, 3H). TOF MS m/z 363, 365 (MH$^+$), 385, 387 (M+Na$^+$).

1-(4-Chlorophenyl)-3-[(4-chlorophenyl)amino]-2-(3-methyl-5-isoxazolyl)-2-propen-1-one: $^1$H NMR (400 MHz, CDCl$_3$), δ 12.30 (d, 1H), 8.00 (d, 1H), 7.70 (d, 2H), 7.50 (d, 2H), 7.45 (d, 2H), 7.10 (d, 2H), 7.40 (d, 4H), 5.40 (s, 1H), 2.20 (s, 3H). TOF MS m/z 373, 375 (MH$^+$), 395, 397 (M+Na$^+$).

1-(2-Chlorophenyl)-3-[(4-chlorophenyl)amino]-2-(3-methyl-5-isoxazolyl)-2-propen-1-one. TOF MS ES+ m/z 395 (M+Na$^+$).

EXAMPLE 7

N-(4-Chlorophenyl)-α-[[(4-chlorophenyl)amino]methylene]-2-methyl-2H-tetrazole-2-acetamide

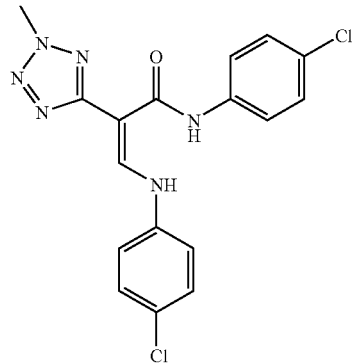

a. Ethyl 2-methyl-2H-tetrazole-5-acetate. A solution of ethyl 1H-tetrazole-5-acetate (Aldrich, powdered with mortar and pestle; 1.01 g, 6.47 mmol) in 100 mL of CH$_3$CN was treated with solid K$_2$CO$_3$ (2.25 g, 16.3 mmol) and iodomethane (1.0 mL, 2.27 g, 16.0 mmol). The resulting mixture was heated at reflux for 8 h. Once at rt, the mixture was filtered and the mother liquor conc. in vacuo. The residue was triturated with CH$_2$Cl$_2$, filtered and conc. to dryness. The resulting mobile orange liquid was dissolved in 1:1 EtOAc/hexanes with the addition of a small volume of CH$_2$Cl$_2$ and added to 19 cm of flash silica gel in a 5 cm dia. column. Elution with 2 L of 3:2 EtOAc/hexanes afforded 409 mg (37%) of the title compound as a light yellow oil. $^1$H NMR (400 MHz, CDCl$_3$) δ 4.33 (s, 3H), 4.20 (q, 2H, J=7.3 Hz), 3.95 (s, 2H), 1.26 (t, 3H, J=7.2 Hz). Further elution with 3:2 EtOAc/hexanes afforded 371 mg (34%) of ethyl 1-methyl-1H-tetrazole-5-acetate as a white solid. $^1$H NMR (400 MHz, CDCl$_3$) δ 4.22 (q, 2H, J=7.1 Hz), 4.07 (s, 3H), 4.03 (s, 2H), 1.28 (t, 3H, J=7.0 Hz).

b. 2-Methyl-2H-tetrazole-5-acetic acid. To a solution of ethyl 2-methyl-2H-tetrazole-5-acetate (399 mg, 2.34 mmol) in 5 mL of EtOH was added 3.5 mL of a 1M aq. NaOH solution. After stirring at rt for 2 h, the reaction was diluted with 10 mL of a 1M aq. HCl solution and extracted with EtOAc (3×20 mL). The pooled organic layers were washed with brine, dried (Na$_2$SO$_4$), filtered and conc. to 279 mg (84%) of the desired acid which was carried on without purification.

c. N-(4-Chlorophenyl)-2-methyl-2H-tetrazole-2-acetamide. A solution of acid prepared above (125 mg, 0.88 mmol) in 2 mL of dry THF was treated with solid carbonyl diimidazole (146 mg, 0.90 mmol). After 1 h at rt, 114 mg (0.89 mmol) of 4-chloroaniline was added in one portion. After stirring overnight, the reaction was diluted with 10 mL of EtOAc and washed with an aq. 1M HCl solution (10 mL), 6 mL of an aq. 1M NaOH solution and brine. After drying (Na$_2$SO$_4$) and filtration, the solvent was removed in vacuo to give 176 mg (80%) of the desired amide as a light yellow solid. $^1$H NMR (400 MHz, CDCl$_3$) δ 8.62 (br s, 1H), 7.49 (d, 2H, J=8.8 Hz), 7.27 (d, 2H, J=8.8 Hz), 4.38 (s, 3H), 4.05 (s, 2H). TOF MS m/z 274 (M+Na$^+$).

d. N-(4-Chlorophenyl)-α-hydroxylmethylene-2-methyl-2H-tetrazole-2-acetamide. Sodium hydride (Aldrich, 60% dispersion in mineral oil; 60 mg, 1.5 mmol) was suspended in 3 mL of dry THF and solid N-(4-chlorophenyl)-2-methyl-2H-tetrazole-2-acetamide (143 mg, 0.57 mmol) was added in one portion. Gas evolved and the resulting mixture was stirred at rt for 30 mins. Neat ethyl formate (0.25 mL, 230 mg, 3.11 mmol) was added dropwise via syringe. After stirring overnight, the reaction was added to ice and 10 mL of 1N aq HCl. A ppt formed and the mixture was extracted with EtOAc (3×15 mL). The organic layers were pooled, washed with brine, dried (Na$_2$SO$_4$), filtered and concentrated. Trituration with hexanes gave 135 mg (85%) of the desired compound as a pink solid. $^1$H NMR (400 MHz, CDCl$_3$) δ 15.09 (d, 1H, J=11.6 Hz), 10.60 (br s, 1H), 8.48 (d, 1H, J=11.3 Hz), 7.61 (d, 2H, J=8.8 Hz), 7.34 (d, 2H, J=8.8 Hz), 4.38 (s, 3H).

e. N-(4-Chlorophenyl)-α-[[(4-chlorophenyl)amino]methylene]-2-methyl-2H-tetrazole-2-acetamide. A solution of N-(4-chlorophenyl)-α-hydroxymethylene-2-methyl-2H-tetrazole-2-acetamide (31.7 mg, 0.113 mmol) in 2 mL of benzene was treated with solid 4-chloroaniline (16.6 mg, 0.13 mmol). After heating at reflux for 4 h, the reaction was partitioned between 10 mL of EtOAc and 10 mL of aq. 1M HCl. The organic layer was separated, washed with brine, dried (Na$_2$SO$_4$), filtered and conc. The residue was adsorbed onto 300 mg of silica gel and added to 11.5 cm of flash silica gel in a 2 cm dia. column. Elution with 2:1 hexanes/EtOAc afforded 19 mg (43%) of the title compound as a light yellow solid. $^1$H NMR (2.3:1 ratio of isomers; major isomer NMR given, 400 MHz, CDCl$_3$) δ 11.82 (d, 1H, J=13.1 Hz), 10.61 (br s, 1H), 8.49 (d, 1H, J=12.8 Hz), 7.58 (d, 2H, J=8.8 Hz), 7.30-7.27 (m, 4H), 7.06 (d, 2H, J=9.1 Hz), 4.34 (s, 3H).

N-(4-Chlorophenyl)-1-methyl-1H-tetrazole-2-acetamide was prepared as described for the 2-isomer. $^1$H NMR (400 MHz, CDCl$_3$) δ 9.16 (br s, 1H), 7.50 (d, 2H, J=9.1 Hz), 7.29 (d, 2H, J=9.1 Hz), 4.17 (s, 3H), 4.07 (s, 2H).

EXAMPLE 8

N-(4-Chlorophenyl)-α-[[4-(chlorophenyl)amino]methylene]-5-methyl-3-isoxazoleacetamide

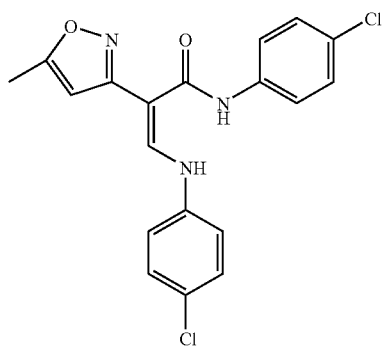

a. 3-Hydroxymethyl-5-methylisoxazole. A solution of methyl 5-methylisoxazole-3-carboxylate (Aldrich; 14.12 g, 100 mmol) in dry THF (150 mL) was cooled in a dry ice/isopropanol bath to −75° C. and the resulting white suspension was treated with 105 mL (105 mmol) of a 1M lithium aluminum hydride solution in THF at such a rate that the internal temperature remained below −55° C. The resulting yellow solution was allowed to warm to rt overnight, recooled in a dry ice/isopropanol bath and treated carefully with cold water added dropwise until no more gas evolved and then acidified with an aqueous 6N HCl solution to pH 1-2. The mixture was conc. in vacuo and the residue was dissolved in toluene and reconc. to dryness. The residue was washed with CHCl$_3$ (3×100 mL), the CHCl$_3$ solution was filtered to remove a small amount of solid, then evaporated to give 8.34 g (74%) of the alcohol as a light yellow oil. $^1$H NMR (400 MHz, CDCl$_3$) δ 6.02 (s, 1H), 4.66 (s, 2H), 2.80-3.10 (m, 1H), 2.39 (s, 3H).

b. 3-Chloromethyl-5-methylisoxazole. To a solution of 3-hydroxymethyl-5-methyl-isoxazole obtained above (8.34 g, 74 mmol) in CH$_2$Cl$_2$ (80 mL) was added 11 mL of SOCl$_2$ dropwise at rt with stirring. The solution was stirred at rt for 1 h and then heated at reflux for 20 mins. The reaction was evaporated to dryness and the residual dark oil was purified by chromatography (4/1 hexane:EtOAc) to give 6.40 g (66%) of the title chloride as a yellow semi-solid. $^1$H NMR (400 MHz, CDCl$_3$) δ 6.05 (s, 1H), 4.49 (s, 2H), 2.38 (s, 3H).

c. 3-Cyanomethyl-5-methylisoxazole. To a solution of 3-chloromethyl-5-methy-lisoxazole (6.0 g, 45 mmol) in CH$_2$Cl$_2$ (80 mL) was added a solution of NaCN (22 g) and benzyltriethylammonium chloride (1.1 g) in water (50 mL). After heating at reflux for 16 h the reaction was allowed to cool to rt and the organic layer was separated. The aqueous layer was then extracted with CH$_2$Cl$_2$ (50 mL). The CH$_2$Cl$_2$ extracts were combined, washed with brine, dried (Na$_2$SO$_4$), filtered and evaporated and the residue was purified by chromatography (3/2 hexane:EtOAc) affording 1.51 g (24%) of 3-cyanomethyl-5-methylisoxazole as a white solid, mp. 38-39° C. $^1$H NMR (400 MHz, CDCl$_3$) δ 6.07 (s, 1H), 3.73 (s, 2H), 2.42 (s, 3H).

d. 5-Methyl-3-isoxazoleacetic acid. To a solution of 3-cyanomethyl-5-methylisoxazole (1.50 g, 12.3 mmol) in AcOH (15 mL) was added 20 mL of conc. aqueous HCl and the resulting mixture was stirred at 80-85° C. for 17 h. Once at rt, the reaction was conc. to dryness and the residue was extracted with CH$_2$Cl$_2$ (3×50 mL). The CH$_2$Cl$_2$ extracts were combined, washed with brine, dried (Na$_2$SO$_4$), filtered and conc. in vacuo. The solid was triturated with hexanes, affording 1.3 g (75%) of the acid as an off-white solid. $^1$H NMR (400 MHz, CDCl$_3$) δ 6.06 (s, 1H), 3.77 (s, 2H), 2.42 (s, 3H).

e. N-(4-Chlorophenyl)-5-methyl-3-isoxazoleacetamide. To a solution of 5-methyl-3-isoxazoleacetic acid (808 mg, 5.67 mmol) in CH$_2$Cl$_2$ (50 mL) was added 1 mL of SOCl$_2$ dropwise at rt with stirring. After 25 mins. at reflux, the reaction was evaporated to dryness and the residue was dissolved in toluene and conc. in vacuo. This residue was dissolved in CH$_2$Cl$_2$ (20 mL) and added dropwise to a solution of 4-chloroaniline (0.75 g, 5.90 mmol) in CH$_2$Cl$_2$ (20 mL). After 5 h at rt the reaction was filtered and the filtrate was evaporated and purified by chromatography (7/3 CH$_2$Cl$_2$:EtOAC) to give 0.88 g (61%) of the isoxazoleacetamide as a white solid. $^1$H NMR (400 MHz, CDCl$_3$) δ 8.26 (s, 1H), 7.47 (d, 2H, J=6.6 Hz), 7.27 (d, 2H, J=6.6 Hz), 6.07 (s, 1H), 3.77 (s, 2H), 2.45 (s, 3H).

f. N-(4-Chlorophenyl)-α-[[4-(chlorophenyl)amino]methylene]-5-methyl-3-isoxazoleacetamide. To a solution of N-(4-chlorophenyl)-5-methyl-3-isoxazoleacetamide (440 mg, 1.76 mmol) in dry THF (20 mL) at 0° C. was added NaH (60% in oil) in small portions. The resulting mixture was stirred cold for 1 h, and neat ethyl formate (300 mg, 3.00 mmol) was added and the reaction was stirred for 16 h and quenched with cold water. The pH was brought to 1-2 with an aqueous 6N HCl solution and evaporated to dryness. The residue was extracted with CH$_2$Cl$_2$ (50 mL) and the CH$_2$Cl$_2$ extract was washed with brine, dried (Na$_2$SO$_4$), filtered and evaporated to dryness. The residue was dissolved in CH$_2$Cl$_2$ (10 mL) and added to a solution of 4-chloroaniline (300 mg) in CH$_2$Cl$_2$ (20 mL). After stirring at rt for 5 h the solvent was removed in vacuo and the residue was purified by chromatography on silica gel. Elution with 7/3 hexane:EtOAc afforded 22 mg (3%) of the title compound as a light yellow solid, mp 179-180° C. $^1$H NMR (400 MHz, CDCl$_3$) δ 11.84 (d, 1H, J=9.0 Hz), 10.60 (s, 1H), 7.66 (d, 1H, J=9.0 Hz), 7.60 (d, 2H, J=6.0 Hz), 7.32-7.30 (dd, 4H, J=6.0, 1.5 Hz), 7.02 (d, 2H, J=7.0 Hz), 6.09 (s, 1H), 2.46 (s, 3H). TOF MS ES+ m/z 388, 390 (M+H$^+$).

By using the procedure described above for N-(4-chlorophenyl)-α-[[4-(chlorophenyl)-amino]methylene]-5-methyl-3-isoxazoleacetamide, the following compounds were similarly prepared:

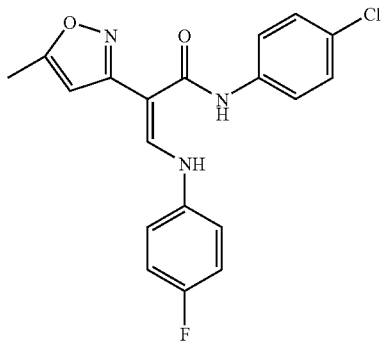

N-(4-Chlorophenyl)-α-[[4-(fluorophenyl)amino]methylene]-5-methyl-3-isoxazole-acetamide. Mp 170-170.5° C. ¹H NMR (400 MHz, CDCl₃) δ 11.80 (d, 1H, J=9.0 Hz), 10.60 (s, 1H), 7.64 (d, 1H, J=9.0 Hz), 7.60 (d, 2H, J=6.0 Hz), 7.31 (d, 2H, J=6.6 Hz), 7.26-7.05 (m, 4H), 6.07 (s, 1H), 2.45 (s, 3H). TOF MS ES+ m/z 396, 398 (M+Na⁺).

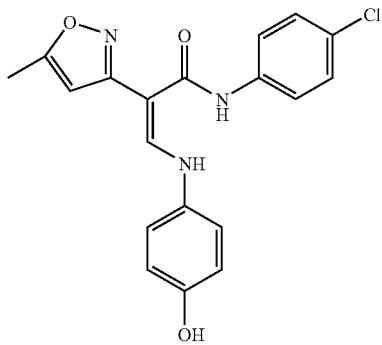

N-(4-Chlorophenyl)-α-[[4-(hydroxyphenyl)amino]methylene]-5-methyl-3-isoxazole-acetamide. Mp. 223° C. ¹H NMR (400 MHz, CDCl₃) δ 11.70 (d, 1H, J=9.0 Hz), 10.55 (s, 1H), 7.60 (d, 1H, J=9.0 Hz), 7.57 (d, 2H, J=6.0 Hz), 7.27 (s, 2H), 6.96 (d, 2H, J=6.0 Hz), 6.81 (d, 2H, J=6.0 Hz), 6.03 (s, 1H), 2.41 (s, 3H). TOF MS ES+ m/z 392, 394(M+Na⁺).

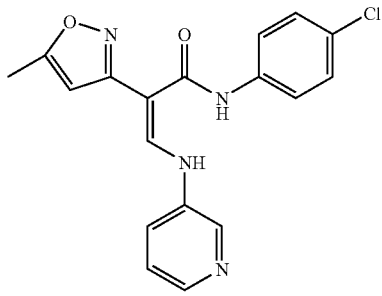

N-(4-Chlorophenyl)-α-[(3-pyridylamino)methylene]-5-methyl-3-isoxazoleacetamide. ¹H NMR (400 MHz, CDCl₃) δ 12.10 (d, 1H, J=9.0 Hz), 10.66 (s, 1H), 8.73 (s, 1H), 8.31 (s, 1H), 7.90 (d, 1H, J=9.0 Hz), 7.57 (d, 2H, J=6.0 Hz), 7.52 (s, 1H), 7.44-7.40 (m, 1H), 7.29 (d, 2H, J=6.0 Hz), 6.27 (s, 1H), 2.44 (s, 3H). TOF MS ES+ m/z 377 (M+Na⁺).

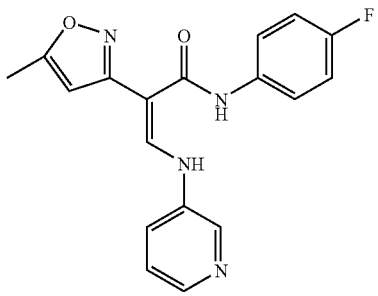

N-(4-Fluorophenyl)-α-[(3-pyridylamino)methylene]-5-methyl-3-isoxazoleacetamide. Mp 181.5-182° C. ¹H NMR (400 MHz, CDCl₃) δ 11.84 (d, 1H, J=9.0 Hz), 10.49 (s, 1H), 7.64 (d, 1H, J=9.0 Hz), 7.57-7.53 (m, 2H), 7.29 (d, 2H, J=6.0 Hz), 7.04-6.97 (m, 4H), 6.06 (s, 1H), 2.43 (s, 3H). TOF MS ES+ m/z 372, 374 (M+H⁺), 394, 396 (M+Na⁺).

EXAMPLE 9

α-[4-(chlorophenylamino)methylene]-3-methyl-N-pyridyl-5-isoxazoleacetamide

General method for synthesis of N-pyridyl-3-methylisoxazoleacetamides: The desired aminopyridine (0.94 g, 10 mmol) was dissolved in 20 mL of THF at 0° C. and treated with DCC (2.06 g, 10 mmol), followed with a solution of 3-methyl-5-isoxazole acetic acid (1.41 g, 10 mmol) in 10 mL of THF. After stirring at rt overnight the solvent was removed in vacuo and the residue was purified by chromatography (10% MeOH/CH₂Cl₂), affording the desired N-pyridyl-3-methyl-5-isoxazoleacetamide.

N-(4-pyridyl)-3-methyl-5-isoxazoleacetamide; 1.1 g (yield 55%). ¹H NMR (400 MHz, CDCl₃) δ 9.33 (s, 1H), 8.46 (d, 2H), 7.66 (d, 2H), 6.15 (s, 1H), 3.94 (s, 2H), 2.25 (s, 3H). TOF MS ES+ m/z 198 (M+H⁺).

N-(2-pyridyl)-3-methyl-5-isoxazoleacetamide; 1.4 g (yield 70%).

N-(3-pyridyl)-3-methyl-5-isoxazoleacetamide; 1.8 g (yield 90%).

General method for the synthesis of α-hydroxymethylene-3-methyl-N-pyridyl-5-isoxazoleacetamide: A solution of N-pyridyl-3-methyl-5-isoxazoleacetamide (1.1 g, 5 mmol) in THF (20 mL) was slowly added to a suspension of NaH (60% in oil; 0.5 g, 12.5 mmol) in 10 mL of THF. The reaction mixture was stirred at rt for 30 mins. and then ethyl formate (2 mL, 25 mmol) was added. After stirring at rt overnight, the reaction was conc. in vacuo and the residue was dissolved in 100 mL of a 1N aqueous NaOH solution and extracted with 25 mL of EtOAc. The aqueous layer was separated and brought to pH 5-6 with the addition of an aqueous 6N HCl solution. The resulting light yellow precipitate was collected and washed with cold water, affording the desired product.

α-Hydroxymethylene-3-methyl-N-(4-pyridyl)-5-isoxazoleacetamide; Isolated as a light yellow solid (yield 60%). ¹H NMR (400 MHz, DMSO-d₆): δ 13.70 (s, 1H), 9.22 (s, 1H), 8.42 (d, 2H), 7.96 (d, 2H), 6.20 (s, 1H), 2.03 (s, 3H).

α-Hydroxymethylene-3-methyl-N-(2-pyridyl)-5-isoxazoleacetamide; 0.7 g (yield 65%).

α-Hydroxymethylene-3-methyl-N-(3-pyridyl)-5-isoxazoleacetamide; 1.1 g (yield 89%).

General method for the synthesis of α-[4-(chlorophenylamino)methylene]-3-methyl-N-pyridyl-5-isoxazoleacetamide: α-Hydroxymethylene-3-methyl-N-pyridyl-5-isoxazoleacetamide (0.25 g, 1.0 mmol) was stirred with 4-chloroaniline (0.13 g, 1.0 mmol) and acetic acid (200 μL) in DMSO (3 mL) at rt for 24 h. The resulting solution was mixed with 10 mL of an aqueous 0.5 N NaOH solution and extracted with CH$_2$Cl$_2$. The organic layer was dried over Na$_2$SO$_4$ filtered and concentrated. The residue was then recrystallized from MeOH.

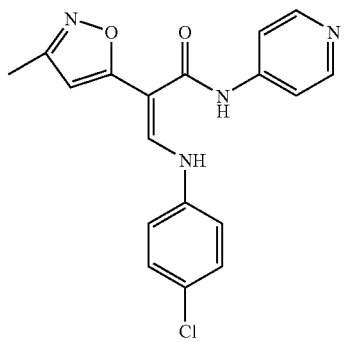

α-[4-(Chlorophenylamino)methylene]-3-methyl-N-(4-pyridyl)-5-isoxazoleacetamide; Isolated as light yellow solid, yield 40%. $^1$H NMR (400 MHz, CDCl$_3$) δ 11.43 (d, 1H), 8.44 (s, 1H), 8.43 (d, 2H), 7.68 (d, 2H), 7.48 (d, 2H), 8.28 (d, 2H), 6.99 (d, 2H), 5.97 (s, 1H), 2.20 (s,3H). TOF MS ES+ m/z 355, 357 (M+H$^+$), 377, 379 (M+Na$^+$).

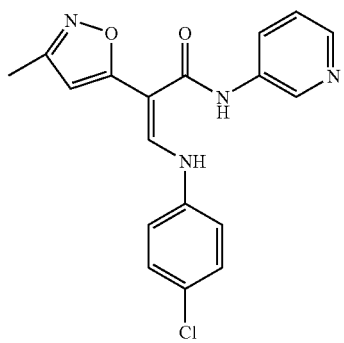

α-[4-(Chlorophenylamino)methylene]-3-methyl-N-(2-pyridyl)-5-isoxazoleacetamide (lot 08wyl080); yield 50%.

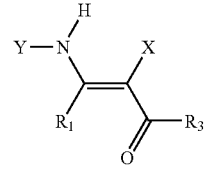

α-[4-(Chlorophenylamino)methylene]-3-methyl-N-(3-pyridyl)-5-isoxazoleacetamide

EXAMPLE 10

Synthesis of N-(4-chlorophenyl)-3-methyl-5-isoxazoleacetamide from 3,5-dimethylisoxazole A solution of 3,5-dimethylisoxazole (Aldrich; 30 mL, 29.7 g, 306 mmol) in 300 mL of dry THF under N$_2$ was cooled in an acetone-dry ice bath for 15 mins. A 2M solution of butyllithium in pentane (Aldrich; 135 mL, 270 mmol) was added dropwise via addition funnel over 1.5 h. A solution of 4-chlorophenylisocyanate (Aldrich; 16.2 mL, 19.4 g, 127 mmol) in 40 mL of dry THF was then added dropwise to the cold reaction over 70 mins. After stirring for 70 mins., the orange-brown solution was quenched with a sat. aq. NH$_4$Cl solution. The resulting solution was diluted with water and extracted with EtOAc (2×50 mL). The pooled organic layers were washed with brine, dried (Na$_2$SO$_4$), filtered and conc. to dryness. The residue was triturated with hexanes (5×100 mL) leaving 29.1 g of a yellow solid. After two recrystallizations from iPrOH, 9.3 g (27% yield) of the desired amide was isolated as a light yellow solid. This material was identical to the amide prepared from 3-methyl-5-isoxazoleacetic acid in Example 2 by $^1$H NMR and TLC.

What is claimed is:

1. A compound of Formula I:

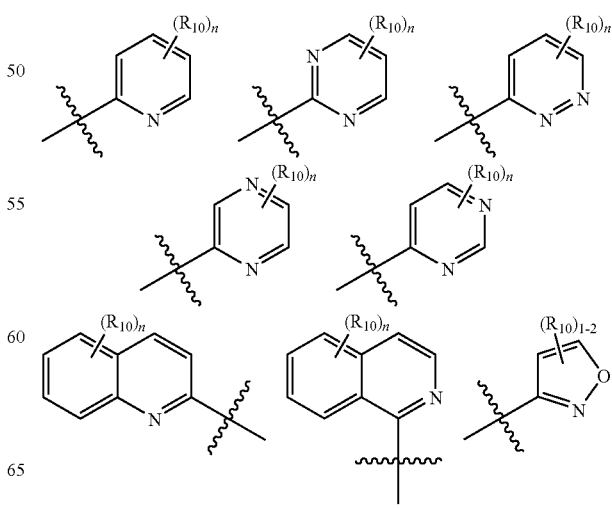

or a pharmaceutically acceptable salt thereof, wherein:

X is an optionally substituted heteroaromatic ring (HET) selected from the group consisting of:

-continued

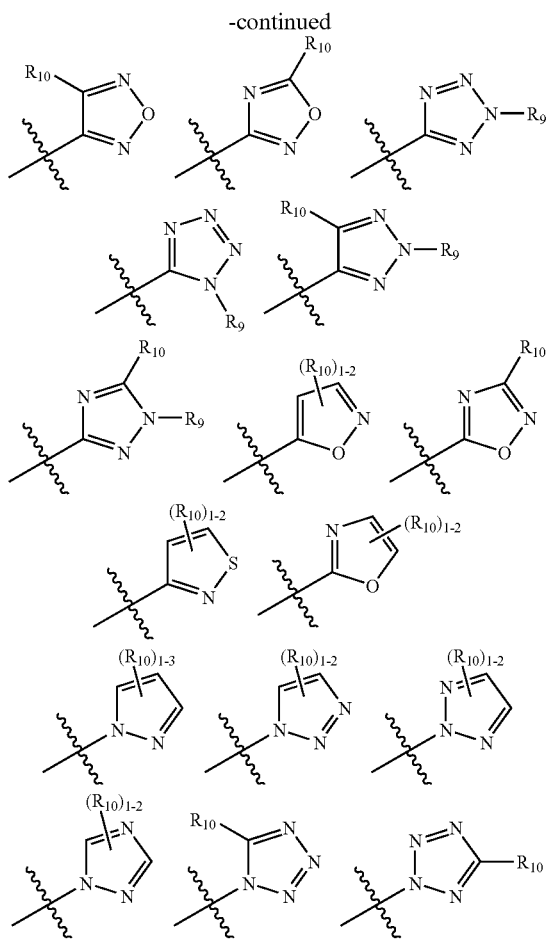

wherein:

n is 0-3;

Y is selected from the group consisting of aryl and heteroaryl, and a dialkylamino group, each unsubstituted or substituted;

$R_1$ is selected from the group consisting of hydrogen and substituted or unsubstituted $C_{1-10}$alkyl;

$R_3$ is selected from the group consisting of arylamino, heteroarylamino and aryl, each unsubstituted or substituted; and each $R_9$ is independently selected from the group consisting of hydrogen, $C_{1-10}$alkyl, aralkyl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

with the proviso that the compound is not 1-phenyl-3-phenylamino-2-(3-methyl-5-isoxazolyl)-2-propen-1-one, 3-[(4-methoxyphenyl)amino]-2-(3-methyl-5-isoxazolyl)-1-phenyl-2-propen-1-one or 1-phenyl-3-phenylamino-2-(2-pyridyl)-2-propen-1-one.

2. The compound of claim 1, wherein said compound is a compound of Formula II:

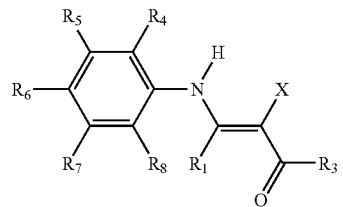

or a pharmaceutically acceptable salt thereof, wherein:

X is an optionally substituted heteroaromatic ring (HET) selected from the group consisting of:

wherein:

n is 0-3;

Y is selected from the group consisting of aryl and heteroaryl, and a dialkylamino group, each unsubstituted or substituted;

R₁ is selected from the group consisting of hydrogen and substituted or unsubstituted $C_{1-10}$alkyl;

R₃ is selected from the group consisting of arylamino, heteroarylamino and aryl, each unsubstituted or substituted;

R₄, R₅, R₆, R₇, and R₈ are each independently selected from the group consisting of hydrogen, halo, halo $C_{1-10}$alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or R₄ and R₅, or R₅ and R₆, or R₆ and R₇, or R₇ and R₃ are taken together with the carbon atoms to which they are attached to form an unsubstituted or substituted fused 5 or 6 membered saturated, partially unsaturated ring optionally interrupted by one —O—, —NR—, —S—, —SO— or —SO₂—, aryl or heteroaryl, where R is hydrogen or unsubstituted or substituted $C_{1-10}$alkyl;

each R₉ is independently selected from the group consisting of hydrogen, $C_{1-10}$alkyl, aralkyl, cycloalkyl and cycloaralkyl, each unsubstituted or substituted; and each R₁₀ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryloxy, heteroaryl, heteroaryloxy, cyano, cycloalkyl and heterocycloalkyl, each unsubstituted or substituted;

with the proviso that the compound is not 1-phenyl-3-phenylamino-2-(3-methyl—S—isoxazolyl)-2-propen-1-one, 3-[(4-methoxyphenyl)amino]-2-(3-methyl—S—isoxazolyl)-1-phenyl-2-propen-1-one or 1-phenyl-3-phenylamino-2-(2-pyridyl)-2-propen-1-one.

3. The compound of claim 1, wherein said compound is a compound of Formula III:

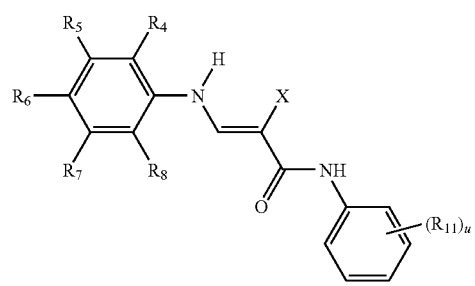

III or a pharmaceutically acceptable salt thereof, wherein:

u is 1-5;

X is an optionally substituted heteroaromatic ring (HET) selected from the group consisting of:

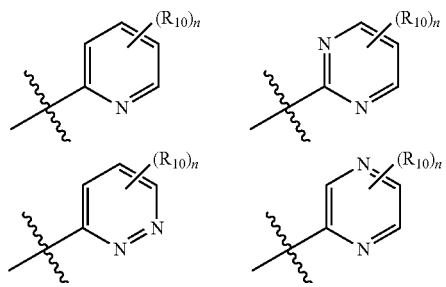

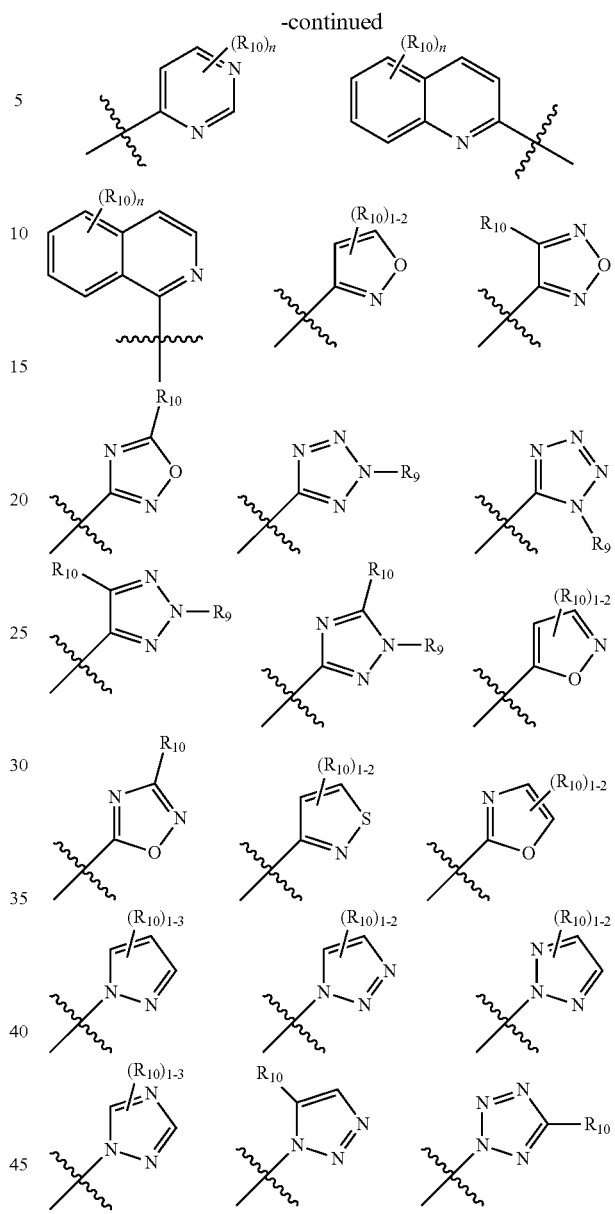

n is 0-3;

R₄, R₅, R₆, R₇, and R₈ are each independently selected from the group consisting of hydrogen, halo, halo $C_{1-10}$alkyl, $C_{1-10}$alkyl, $C_{2-10}$alkynyl, $C_{1-10}$ alkoxy, cycloalkyl, aryl, aryloxy, aryl$C_{1-10}$alkyl and heteroaryl$C_{1-10}$alkyl; or R₄ and R₅, or R₅ and R₆, or R₆ and R₇, or R₇ and R₃ are taken together with the carbon atoms to which they are attached to form an unsubstituted or substituted fused 5 or 6 membered saturated, partially unsaturated ring optionally interrupted by one —O—, —NR—, —S—, —SO— or —SO₂—, aryl or heteroaryl, where R is hydrogen or unsubstituted or substituted $C_{1-10}$alkyl;

each R₉ is independently selected from the group consisting of hydrogen, $C_{1-10}$alkyl, aralkyl, cycloalkyl and cycloaralkyl, each unsubstituted or substituted;

each R₁₀ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted.

4. The compound of claim 1, wherein said compound is a compound of Formula IV:

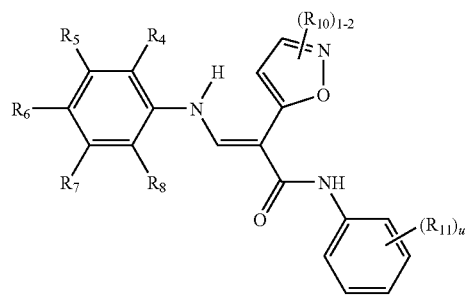

IV or a pharmaceutically acceptable salt thereof, wherein:

$R_4$, $R_5$, $R_6$, $R_7$ and $R_8$ are each independently selected from the group consisting of hydrogen, halo, haloC$_{1-10}$ alkyl, C$_{1-10}$alkyl, C$_{2-10}$alkynyl, C$_{1-10}$ alkoxy, cycloalkyl, aryl, aryloxy, arylC$_{1-10}$alkyl and heteroarylC$_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO—or —SO$_2$—, aryl or heteroaryl, where R is hydrogen or unsubstituted or substituted C$_{1-10}$alkyl;

each $R_{10}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and u is 1-5.

5. The compound of claim 1, wherein said compound is a compound of Formula VI:

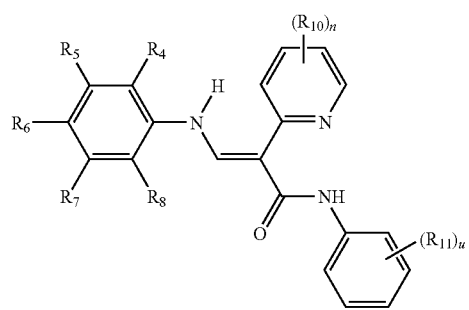

VI or a pharmaceutically acceptable salt thereof, wherein:

$R_4$, $R_5$, $R_6$, $R_7$ and $R_8$ are each independently selected from the group consisting of hydrogen, halo, haloC$_{1-10}$alkyl, C$_{1-10}$alkyl, C$_{2-10}$alknyl, C$_{1-10}$alkoxy, cycloalkyl, aryl, aryloxy, arylC$_{1-10}$alkyl and heteroarylC$_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO—or —SO$_2$—, aryl or heteroaryl, where R is hydrogen or unsubstituted or substituted C$_{1-10}$alkyl;

each $R_{10}$ is independently selected from the group consisting of hydrogen, halogen, haloC$_1$.10alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_1$10alkyl, hydroxyl, C$_{1-10}$alkyl, C$_{2-10}$alkynl, C$_{1-10}$alkoxy, aralkyl, aryl, aryloxy, heteroaryl, heteroaryloxy, cyano, cycloalkyl and heterocycloalkyl, each unsubstituted or substituted;

n is 0 to 3; and u is 1 to 5.

6. The compound of claim 1, wherein said compound is a compound of Formula VII:

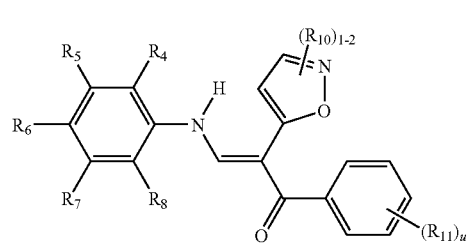

VII or a pharmaceutically acceptable salt thereof, wherein:

$R_4$, $R_5$, $R_6$, $R_7$ and $R_8$ are each independently selected from the group consisting of hydrogen, halo, haloC$_{10}$alkyl, C$_{1-10}$alkyl, C$_{2-10}$alkynyl, C$_{1-10}$alkoxy, cycloalkyl, aryl, aryloxy, arylC$_{1-10}$alkyl and heteroarylC$_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO—or —SO$_2$—, aryl or heteroaryl, where R is hydrogen or unsubstituted or substituted C$_{1-10}$alkyl;

each $R_{10}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and u is 1-5;

with the proviso that the compound is not 3-(phenylamino)-2-(3-methyl-5-isoxazolyl)-1-phenyl-2-propenl-one or 3-[(4-methoxyphenyl)amino]-2-(3-methyl-5-isoxazolyl)-1-phenyl 2-propen-1-one.

7. A compound of claim 1, wherein the compound is:
α-[(3-azabicyclo[3.3.0]octyl-3-amino)methylene]-N-(4-chlorophenyl)-3-methyl-5-isoxazoleacetamide;
N-(4-chlorophenyl)-α-[(3-methylisoxazol-5-ylamino)methylene]-3-methyl-5-isoxazoleacetamide
N-(4-chlorophenyl)-3-methyl-α-[(5-methylisoxazol-3-ylamino)methylene]-5-isoxazoleacetamide;
N-(4-fluorophenyl)-3-methyl-α-[(5-methylisoxazol-3-ylamino)methylene]- 5-isoxazoleacetamide;
N-(4-chlorophenyl)-α-[[4-(chlorophenyl)amino]methylene]-5-methyl-3-isoxazoleacetamide;
N-(4-chlorophenyl)-α[[4-(fluorophenyl)amino]methylene]-5-methyl-3-isoxazoleacetamide;
N-(4-chlorophenyl)-α[[4-(hydroxyphenyl)amino]methylene]-5-methyl-3-isoxazoleacetamide;
N-(4-chlorophenyl)-α[(3-pyridylamino)methylene]-5-methyl-3-isoxazoleacetamide; or
N-(4-fluorophenyl)-α-[(3-pyridylamino)methylene]-5-methyl-3-isoxazoleacetamide.

8. The compound of claim 2, wherein:
R₁ is hydrogen;
R₃ is arylamino; and
R₆ is ethoxy or chloro.

9. A compound of claim 2, wherein the compound is:
3-[(4-ethoxyphenyl)amino]-2-(3-methyl-5-isoxazolyl)-1-phenyl-2-propen-1-one;
3-[(4-hydroxyphenyl)amino]-2-(3-methyl-5-isoxazolyl)-1-phenyl-2-propen-1-one;
3[(4-chlorophenyl)amino]-2-(3-methyl-5-isoxazolyl)-1-phenyl-2-propen-1-one;
α-[4-(chlorophenylamino)methylene]-3-methyl-N-(4-pyridyl)-5-isoxazoleacetamide;
α-[4-(chlorophenylamino)methylene]-3-methyl-N-(2-pyridyl)-5-isoxazoleacetamide; or
α-4-(chlorophenylamino)methylene]-3-methyl-N-(3-pyridyl)-5-isoxazoleacetamide.

10. A compound of claim 4, wherein said compound is:
α-[[(4-iodophenyl)amino]methylene]-3-methyl-N-phenyl-5-isoxazoleacetamide;
α-[[(4-ethoxyphenypamino]methylene]-3-methyl-N-phenyl-5-isoxazoleacetamide;
N-(4-chlorophenyl)-α-[[(4-ethoxyphenyl)amino]methylene]-3-methyl-5-isoxazoleacetamide;
N-(3-chlorophenyl)-α-[[(4-ethoxyphenyl)amino]methylene]-3-methyl-5-isoxazoleacetamide;
N-(2-chlorophenyl)-α-[[(4-ethoxyphenyl)amino]methylene]-3-methyl-5-isoxazoleacetamide;
N-(4-chlorophenyl)-α-[[(4-chlorophenyl)amino]methylene]-3-methyl-5-isoxazoleacetamide;
N-(4 -chlorophenyl)-α-[(3-fluorophenyl)amino)methylene]-3-methyl-5-isoxazoleacetamide;
N-(4-chlorophenyl)-α-[(1 H-indol-5-ylamino)methlene]-3-methyl-5-isoxazoleacetamide;
N-(4-chlorophenyl)-α-[(3 -hydroxylphenylamino)methylene]-3-methyl-5-isoxazoleacetamide;
N-(4-chlorophenyl)-α-[(isoquinolin-5-ylamino)methylene]-3-methyl-5-isoxazoleacetamide;
N-(4-chlorophenyl)-α-[(indazol-6-ylamino)methylene]-3-methyl-5-isoxazoleacetamide;
N-(4-chlorophenyl)-α-[(indazol-5-ylamino)methylene]-3-methyl-5-isoxazoleacetamide;
N-(4-chlorophenyl)-3-methyl-α-[(4-nitrophenylamino)methylene]-5-isoxazoleacetamide;
N-(4-chlorophenyl)-α-[[(4-dimethylamino)phenylamino]methylene]-3-methyl-5-isoxazoleacetamide;
N-(4-fluorophenyl)-α- [(4-fluorophenylamino)methylene]-3-methyl-5-isoxazoleacetamide;
α-[(4-ethylphenylamino)methylene]-N-(4-fluorophenyl)-3-methyl-5-isoxazoleacetamide; or
N-(4-fluorophenyl)-3-methyl-α-[(4-methylphenylamino)methylene]-5-isoxazoleacetamide.

11. A pharmaceutical composition, comprising a pharmaceutically acceptable carrier or diluent and a compound of Formula I:

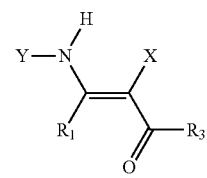

or a pharmaceutically acceptable salt thereof, wherein:
X is selected from the group consisting of:

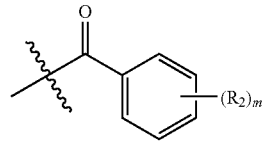

where m is 0 to 5;
an optionally substituted heteroaromatic ring (HET) selected from the group consisting of:

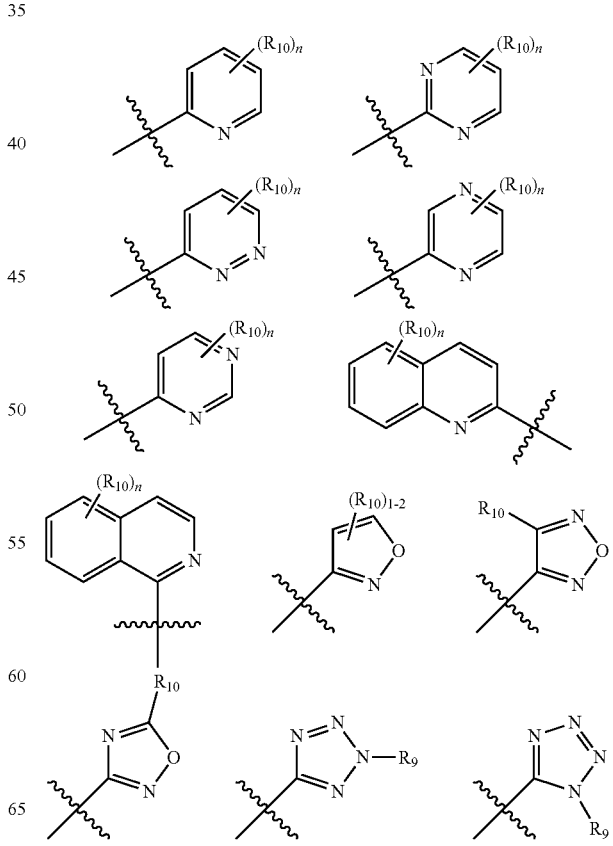

-continued

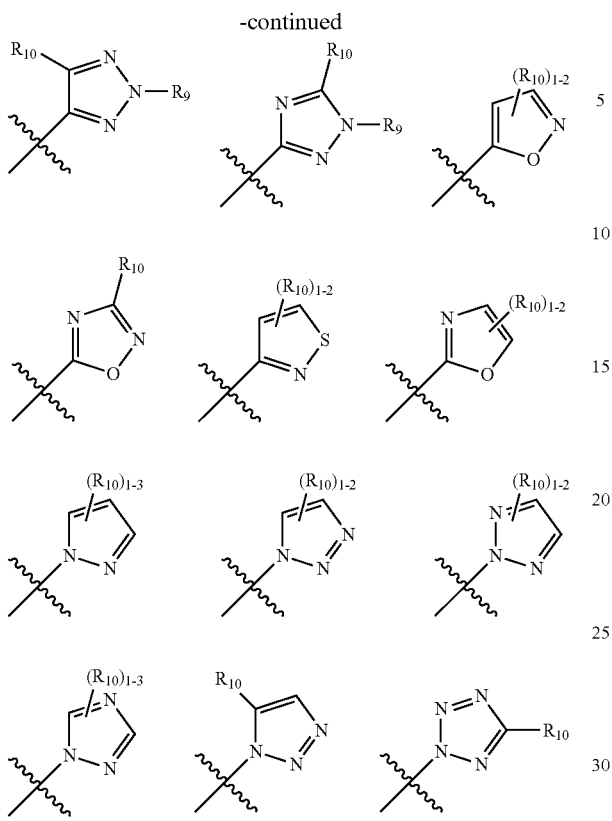

wherein:

n is 0-3;

Y is selected from the group consisting of aryl and heteroaryl, and a dialkylamino group, each unsubstituted or substituted;

$R_1$ is selected from the group consisting of hydrogen and substituted or unsubstituted $C_{1-10}$alkyl;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_3$ is selected from the group consisting of arylamino, heteroarylamino and aryl, each unsubstituted or substituted; and each $R_9$ is independently selected from the group consisting of hydrogen, $C_{1-10}$alkyl, aralkyl, aryl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted.

12. A pharmaceutical composition, comprising a pharmaceutically acceptable carrier or diluent and a compound of Formula III:

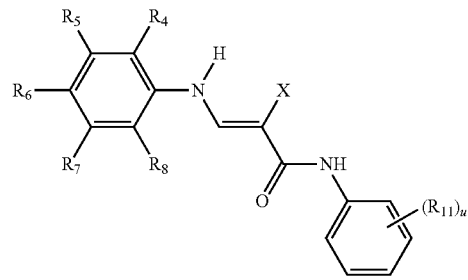

or a pharmaceutically acceptable salt thereof, wherein:

u is 1-5;

X is selected from a group consisting of:

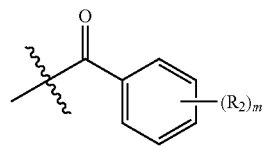

where m is 0 to 5;

an optionally substituted heteroaromatic ring (HET) selected from the group consisting of:

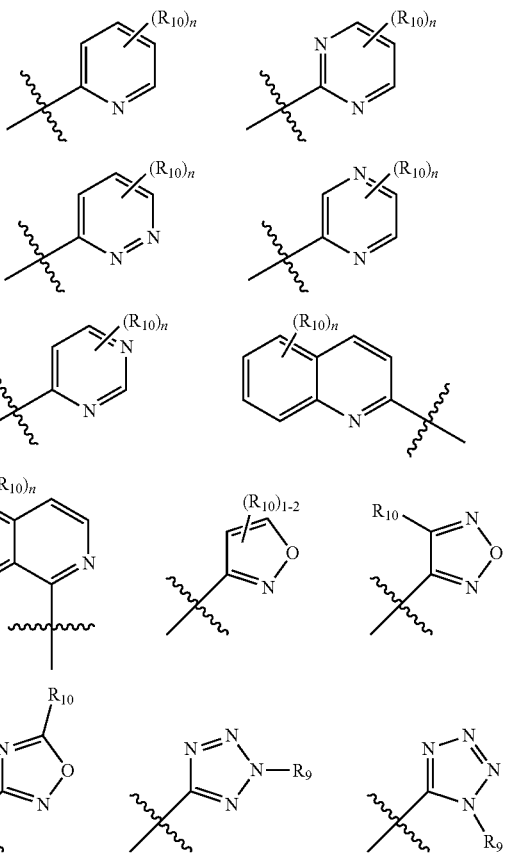

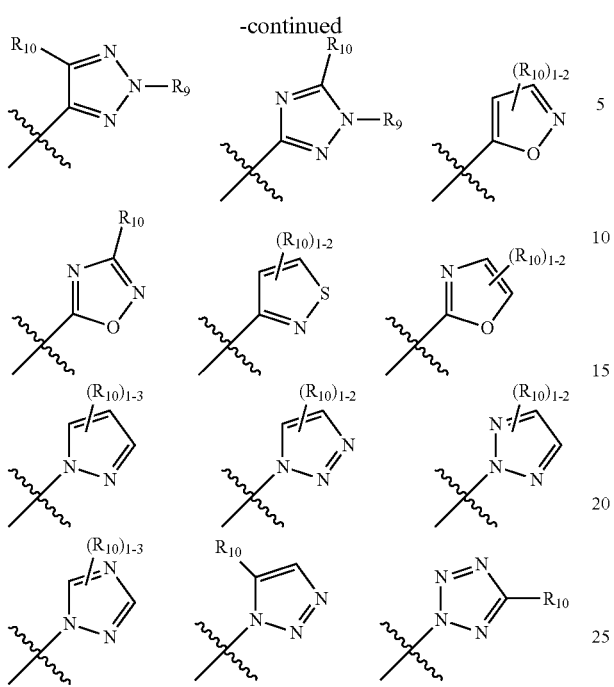

n is 0-3;

Y is selected from the group consisting of aryl and heteroaryl, and a dialkylamino group, each unsubstituted or substituted;

$R_1$ is selected from the group consisting of hydrogen and substituted or unsubstituted $C_{1-10}$alkyl;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_3$ is selected from the group consisting of arylamino, heteroarylamino and aryl, each unsubstituted or substituted;

$R_4$, $R_5$, $R_6$, $R_7$, and $R_8$ are each independently selected from the group consisting of hydrogen, halo, halo $C_{1-10}$alkyl, $C_{1-10}$alkyl, $C_{2-10}$alkynyl, $C_{1-10}$alkoxy, cycloalkyl, aryl, aryloxy, aryl$C_{1-10}$ alkyl and heteroaryl$C_{1-10}$alkyl; or $R_4$ and $R_5$, or $R_5$ and $R_6$, or $R_6$ and $R_7$, or $R_7$ and $R_3$ are taken together with the carbon atoms to which they are attached to form an unsubstituted or substituted fused 5 or 6 membered saturated, partially unsaturated ring optionally interrupted by one —O—, —NR—, —S—, —SO— or —SO$_2$—, aryl or heteroaryl, where R is hydrogen or unsubstituted or substituted $C_{1-10}$alkyl;

each $R_9$ is independently selected from the group consisting of hydrogen, $C_{1-10}$alkyl, aralkyl, aryl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted.

13. A method for the treatment of CNS disorders amenable to modulation of the nAChR complex which comprises administering to a patient in need of such treatment a compound of Formula I or a pharmaceutically acceptable salt thereof, wherein:

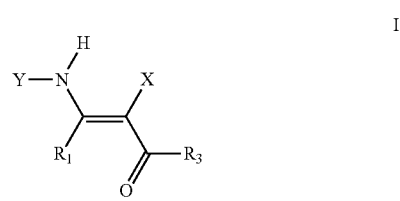

X is selected from the group consisting of:

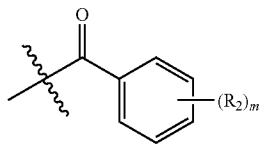

where m is 0 to 5;

an optionally substituted heteroaromatic ring (HET) selected from the group consisting of:

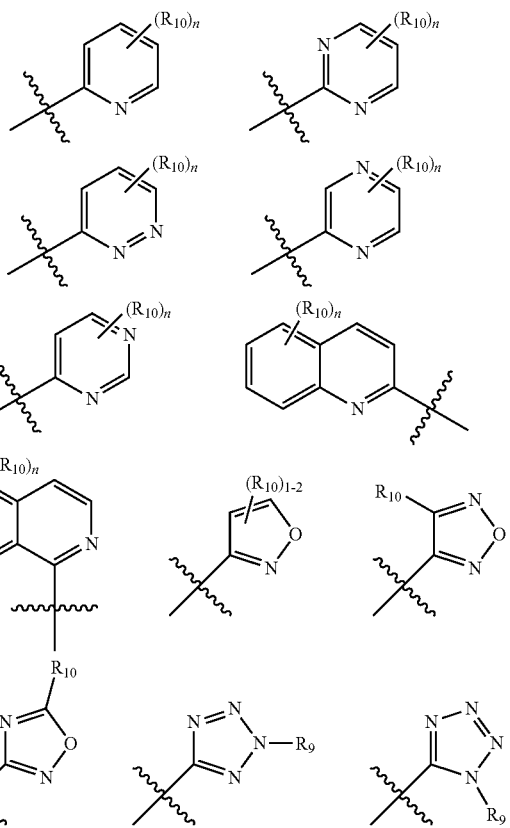

-continued

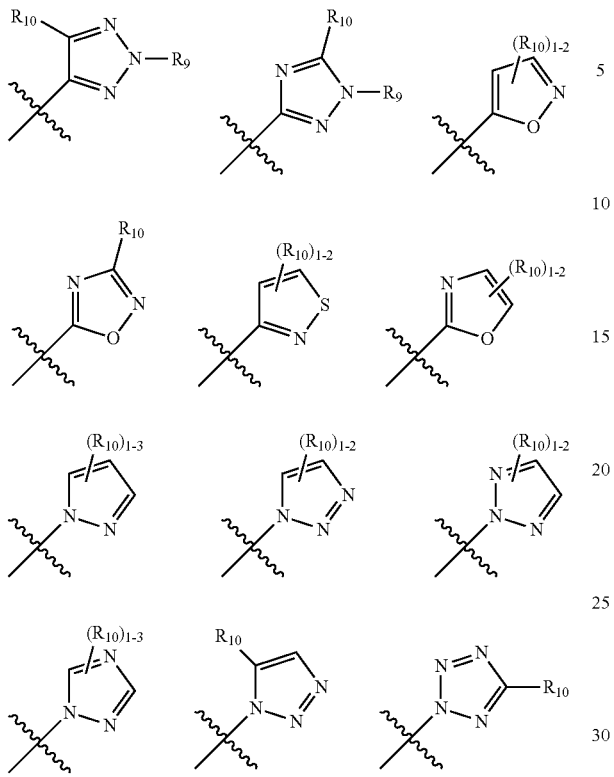

n is 0-3;

Y is selected from the group consisting of aryl and heteroaryl, and a dialkylamino group, each unsubstituted or substituted;

$R_1$ is selected from the group consisting of hydrogen and substituted or unsubstituted $C_{1-10}$alkyl;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_3$ is selected from the group consisting of arylamino, heteroarylamino and aryl, each unsubstituted or substituted; and each $R_9$ is independently selected from the group consisting of hydrogen, $C_{1-10}$alkyl, aralkyl, aryl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkyl, $C_{1-10}$alkoxy, aralkyl, aryl, aryloxy, heteroaryl, heteroaryloxy, cyano, cycloalkyl and heterocycloalkyl, each unsubstituted or substituted.

14. A method for the treatment of CNS disorders amenable to modulation of the nAChR complex which comprises administering to a patient in need of such treatment a compound of Formula III or a pharmaceutically acceptable salt thereof, wherein:

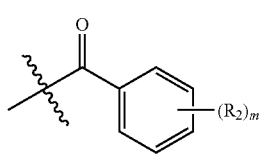

III u is 1-5;
X is selected from a group consisting of:

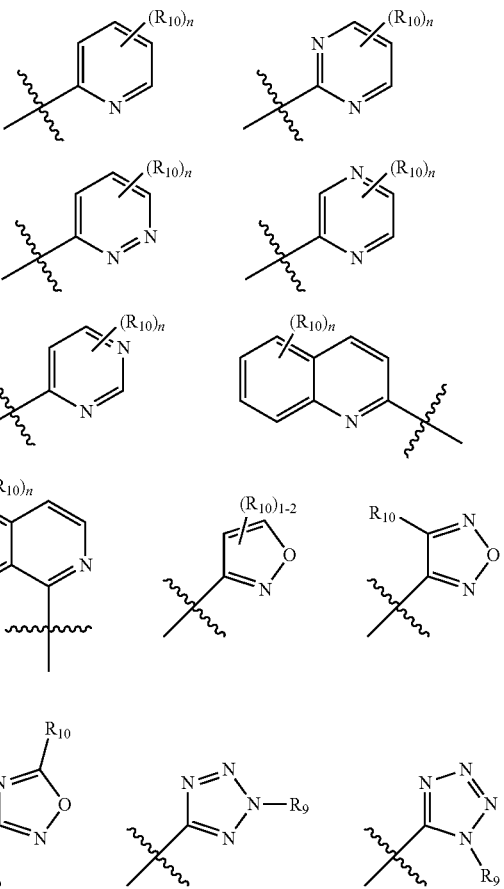

where m is 0 to 5;
an optionally substituted heteroaromatic ring (HET) selected from the group consisting of:

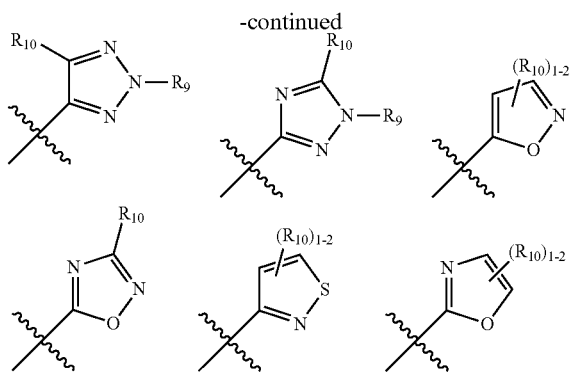

n is 0-3;

each $R_2$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted;

$R_4$, $R_5$, $R_6$, $R_7$, and $R_8$ are each independently selected from the group consisting of hydrogen, halo, halo C$_{1-10}$alkyl, C$_{1-10}$alkyl, C$_{2-10}$alkynyl, C$_{1-10}$alkoxy, cycloalkyl, aryl, aryloxy, arylC$_{1-10}$ alkyl and heteroarylC$_{1-10}$alkyl; or $R_4$ and $R_5$, or $R_5$ and $R_6$, or $R_6$ and $R_7$, or $R_7$ and $R_3$ are taken together with the carbon atoms to which they are attached to form an unsubstituted or substituted fused 5 or 6 membered saturated, partially unsaturated ring optionally interrupted by one —O—, —NR—, —S—, —SO—or —SO$_2$—, aryl or heteroaryl, where R is hydrogen or unsubstituted or substituted C$_{1-10}$alkyl;

each $R_9$ is independently selected from the group consisting of hydrogen, C$_{1-10}$alkyl, aralkyl, aryl, cycloalkyl and cycloaralkyl, each unsubstituted or substituted; and each $R_{10}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted.

15. The method of claim 13, wherein the compound is a compound of Formulae IV:

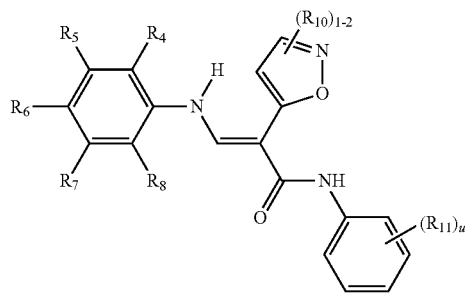

IV or a pharmaceutically acceptable salt thereof, wherein:

$R_4$, $R_5$, $R_6$, $R_7$ and $R_8$ are each independently selected from the group consisting of hydrogen, halo, haloC$_{1-10}$ alkyl, C$_{1-10}$alkyl, C$_{2-10}$alkynyl, C$_{1-10}$alkoxy, cycloalkyl, aryl, aryloxy, arylC$_{1-10}$alkyl and heteroarylC$_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO—or —SO$_2$—, aryl or heteroaryl, where R is hydrogen or unsubstituted or substituted C$_{1-10}$alkyl;

each $R_{10}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and u is 1-5.

16. The method of claim 13, wherein the compound is a compound of Formula VII, or a pharmaceutically acceptable salt thereof, wherein:

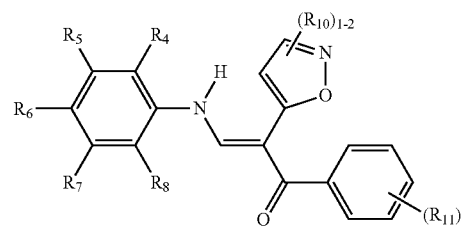

VII $R_4$, $R_5$, $R_6$, $R_7$ and $R_8$ are each independently selected from the group consisting of hydrogen, halo, haloC$_{1-10}$alkyl, C$_{1-10}$alkyl, C$_{2-10}$alkynyl, C$_{1-10}$alkoxy, cycloalkyl, aryl, aryloxy, arylC$_{1-10}$alkyl and heteroarylC$_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO—or —SO$_2$—, aryl or heteroaryl, where R is hydrogen or unsubstituted or substituted C$_{1-10}$alkyl;

each $R_{10}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, haloC$_{1-10}$alkyl, hydroxyl, C$_{1-10}$alkyl, C$_{2-10}$alkynyl, C$_{1-10}$alkoxy, aralkyl, aryl, aryloxy, heteroaryl, heteroaryloxy, cyano, cycloalkyl and heterocycloalkyl, each unsubstituted or substituted; and u is 1-5.

17. The method of claim 13, wherein the CNS disorder is a neurodegenerative disorder.

18. The method of claim 13, wherein the CNS disorder is a senile dementia.

19. The method of claim 13, wherein the CNS disorder is schizophrenia.

20. The method of claim 13, wherein the CNS disorder is a cognition deficit disorder.

21. A method for the treatment of CNS disorders related to learning and memory selected from the group of mild cognitive impairment, age related cognitive decline, senile dementia, and Alzheimer's disease by inhibition of mono and divalent cation conductance through the site mediating the action of compounds of Formula I which comprises administering to a patient in need of such treatment a compound of Formula I or a pharmaceutically acceptable salt thereof, wherein:

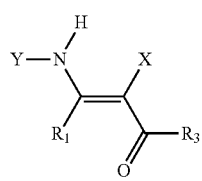

I

X is selected from the group consisting of:

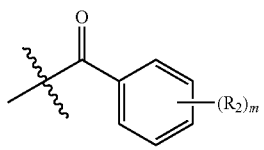

where m is 0 to 5;

an optionally substituted heteroaromatic ring (HET) selected from the group consisting of:

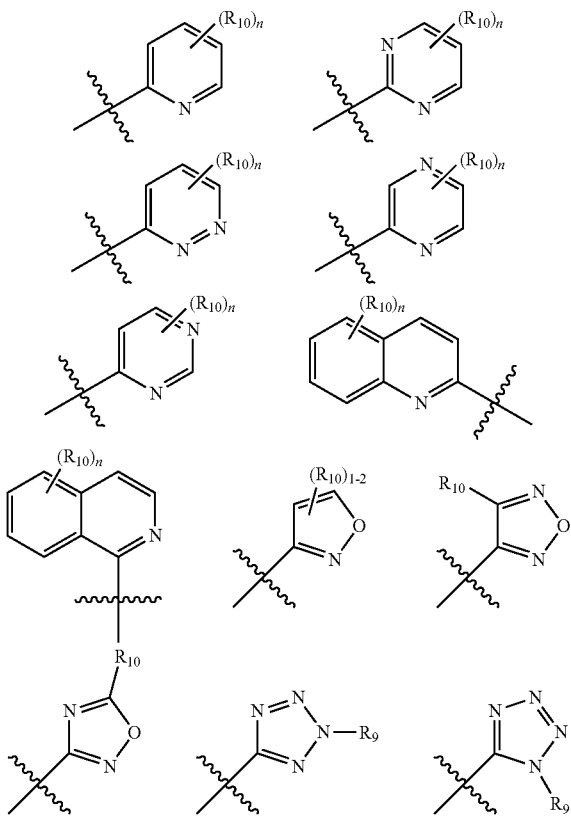

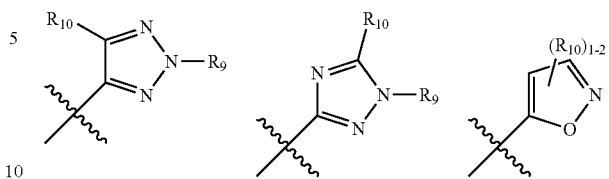

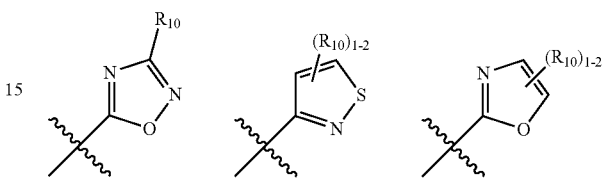

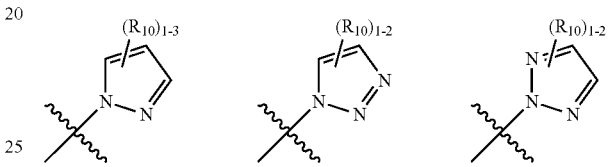

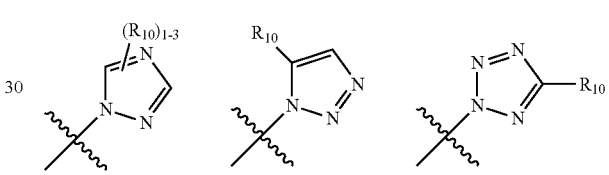

n is 0-3;

Y is selected from the group consisting of aryl and heteroaryl, and a dialkylamino group, each unsubstituted or substituted;

$R_1$ is selected from the group consisting of hydrogen and substituted or unsubstituted $C_{1-10}$alkyl;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_3$ is selected from the group consisting of arylamino, heteroarylamino and aryl, each unsubstituted or substituted; and each $R_9$ is independently selected from the group consisting of hydrogen, $C_{1-10}$alkyl, aralkyl, aryl, cycloalkyl and cycloaralkyl, each unsubstituted or substituted; and each $R_{10}$ is independently selected from the group consisting of hydrogen, halogen, halo$C_{1-10}$alkyl, hydroxyl, $C_{1-10}$alkyl, $C_{2-10}$alkynyl, aralkyl, aryl, aryloxy, heteroaryl, heteroaryloxy, cyano, cycloalkyl and heterocycloalkyl, each unsubstituted or substituted.

22. The method of claim 21, wherein the compound is a compound of Formula III or a pharmaceutically acceptable salt thereof, wherein;

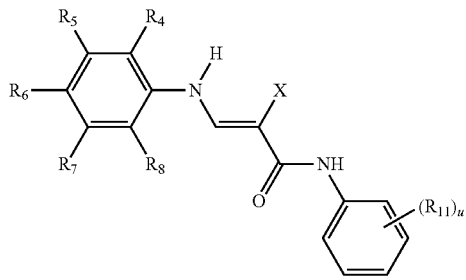

u is 1-5;
X is selected from a group consisting of:

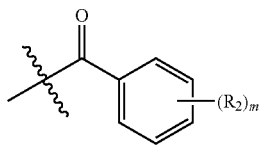

where m is 0 to 5;
an optionally substituted heteroaromatic ring (HET) selected from the group consisting of:

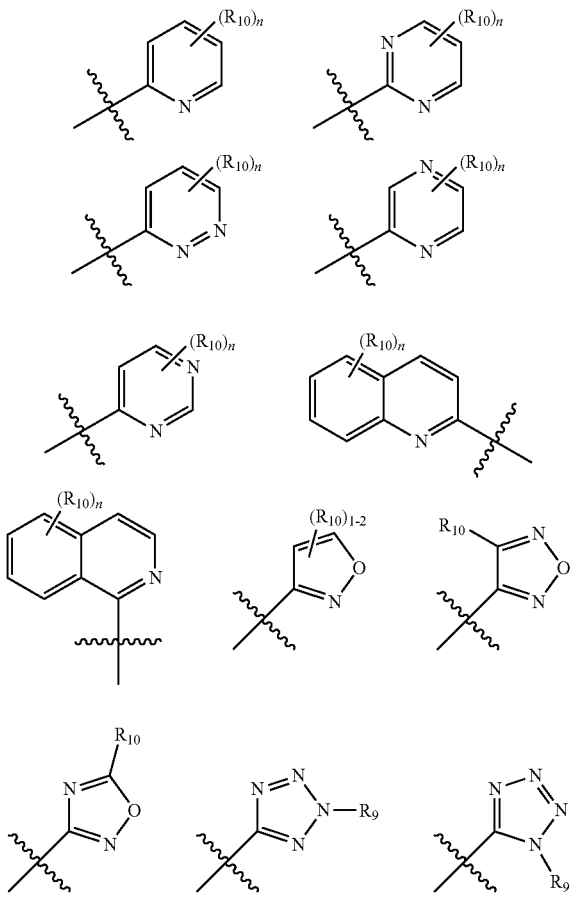

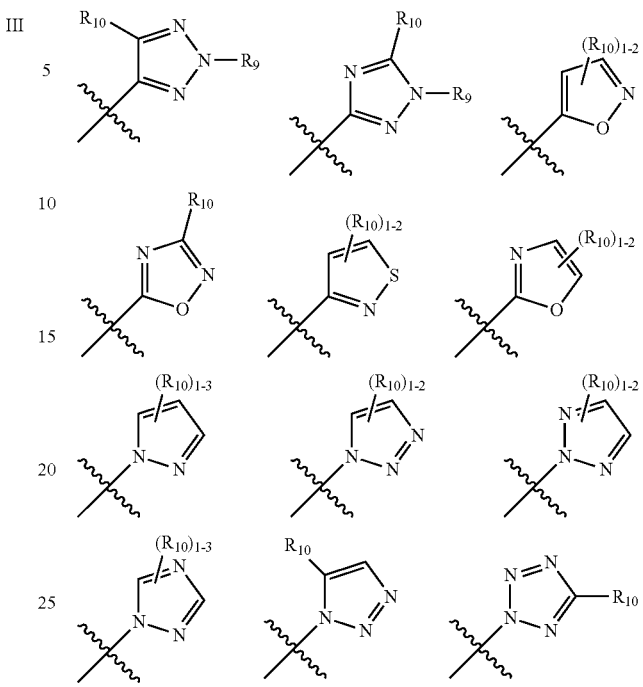

n is 0-3;

each $R_2$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted;

$R_4$, $R_5$, $R_6$, $R_7$, and $R_8$ are each independently selected from the group consisting of hydrogen, halo, halo $C_{1-10}$alkyl, $C_{1-10}$alkyl, $C_{2-10}$alkynyl, $C_{1-10}$alkoxy, cycloalkyl, aryl, aryloxy, aryl$C_{1-10}$ alkyl and heteroaryl$C_{1-10}$alkyl; or $R_4$ and $R_5$, or $R_5$ and $R_6$, or $R_6$ and $R_7$, or $R_7$ and $R_3$ are taken together with the carbon atoms to which they are attached to form an unsubstituted or substituted fused 5 or 6 membered saturated, partially unsaturated ring optionally interrupted by one —O—, —NR—, —S—, —SO— or —SO$_2$—, aryl or heteroaryl, where R is hydrogen or unsubstituted or substituted $C_{1-10}$alkyl;

each $R_9$ is independently selected from the group consisting of hydrogen, $C_{1-10}$alkyl, aralkyl, aryl, cycloalkyl and cycloaralkyl, each unsubstituted or substituted;

each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted.

23. The method of claim 21, wherein the compound is a compound of Formula IV:

![Formula IV structure]

or a pharmaceutically acceptable salt thereof, wherein:
$R_4$, $R_5$, $R_6$, $R_7$ and $R_8$ are each independently selected from the group consisting of hydrogen, halo, halo$C_{1-10}$ alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO— or —SO$_2$—, aryl or heteroaryl, where R is hydrogen or unsubstituted or substituted $C_{1-10}$alkyl;
each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and
each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and
u is 1-5.

24. The method of claim 21, wherein the compound is a compound of Formula VII or a pharmaceutically acceptable salt thereof, wherein:

![Formula VII structure]

$R_4$, $R_5$, $R_6$, $R_7$ and $R_8$ are each independently selected from the group consisting of hydrogen, halo, halo$C_{10}$alkyl, $C_{1-10}$alkyl, $C_{2-10}$alkynyl, $C_{1-10}$alkoxy, cycloalkyl, aryl, aryloxy, aryl$C_{1-10}$alkyl and heteroaryl$C_{1-10}$alkyl; or $R_4$ and $R_5$, or $R_5$ and $R_6$, or $R_6$ and $R_7$, or $R_7$ and $R_8$ are taken together with the carbon atoms to which they are attached to form an unsubstituted or substituted fused 5 or 6 membered saturated, partially unsaturated ring optionally interrupted by one —O—, —NR—, —S—, —SO— or —SO$_2$—, aryl or heteroaryl, where R is hydrogen or unsubstituted or substituted $C_{1-10}$alkyl;
each $R_{10}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and
each $R_{11}$ is independently selected from the group consisting of hydrogen, halogen, halo$C_{1-10}$alkyl, hydroxyl, $C_{1-10}$alkyl, $C_{2-10}$alkynyl, $C_{1-10}$alkoxy, aralkyl, aryl, aryloxy, heteroaryl, heteroaryloxy, cyano, cycloalkyl and heterocycloalkyl, each unsubstituted or substituted; and
u is 1-5.

25. The method of claim 13, wherein the CNS disorder is an anxiety disorder.

26. The method of claim 13, wherein the CNS disorder is convulsions.

27. The method of claim 13, wherein the CNS disorder is insomnia.

28. The method of claim 13, wherein the CNS disorder is a major depressive or bipolar disorder.

29. The method of claim 13, wherein the CNS disorder is chronic or acute pain.

30. The method of claim 13, wherein the CNS disorder is a neuroses.

31. The method of claim 13, wherein the CNS disorder is withdrawal-induced convulsions from substance abuse.

32. The method of claim 13, wherein the CNS disorder is a phobia.

33. The method of claim 13, wherein the CNS disorder is a panic disorder.

34. The method of claim 13, wherein the CNS disorder is a generalized anxiety disorder.

35. The method of claim 13, wherein the CNS disorder is an obsessive-compulsive disorder.

36. The method of claim 13, wherein the CNS disorder is a post traumatic and acute stress disorder.

37. The method of claim 13, wherein the CNS disorder is a migraine.

38. The method of claim 13, wherein the CNS disorder is a bipolar manic disorder.

39. The method of claim 13, wherein the CNS disorder is selected from the group consisting of anxiety and stress related disorders, depression and other affective disorders, epilepsy and other seizure disorders, insomnia and related sleep disorders, acute and chronic pain and cough.

40. The method of claim 39, wherein the sleep disorder involving reduced wakefulness is selected from the group consisting of narcolepsy and idiopathic hypersomnia.

41. The method of claim 13, wherein the compound of Formula I or a pharmaceutically acceptable salt thereof acts by binding to a site that is not the site that binds [$^3$H]-flunitrazepam, barbiturates, loreclezole, [$^3$H]-muscimol or 3α,20α-pregnanediol thereby altering chloride conductance through the GABA$_A$ receptor complex.

42. A method for the treatment of a CNS disorder amenable to modulation of the GABA$_A$ receptor complex which comprises administering to a patient in need of such treatment a compound of claim 1, or a pharmaceutically acceptable salt thereof.

43. A method for the treatment of a CNS disorder which comprises administering to a patient in need of such treatment a compound of claim 1, or a pharmaceutically acceptable salt thereof, wherein said compound exhibits allosteric modulatory activity at both GABA$_A$ and α7 nAChR receptors.

44. A method for the treatment of a CNS disorder which comprises administering to a patient in need of such treatment a compound of claim 1, or a pharmaceutically acceptable salt thereof, with activity for positive allosteric modulation of currents at α7 nAChR receptors in which modulated currents retain the rapid native kinetics and native desensitization of the receptor observed in the absence of a compound of claim 1.

* * * * *